(12) United States Patent
Raghavan

(10) Patent No.: US 9,034,383 B2
(45) Date of Patent: *May 19, 2015

(54) POLICOSANOL NANOPARTICLES

(75) Inventor: Palayakotai R. Raghavan, Chappaqua, NY (US)

(73) Assignee: NanoRx, Inc., Chappaqua, NY (US)

( * ) Notice: Subject to any disclaimer, the term of this patent is extended or adjusted under 35 U.S.C. 154(b) by 149 days.

This patent is subject to a terminal disclaimer.

(21) Appl. No.: 13/211,132

(22) Filed: Aug. 16, 2011

(65) Prior Publication Data

US 2012/0045482 A1    Feb. 23, 2012

Related U.S. Application Data

(60) Provisional application No. 61/376,645, filed on Aug. 24, 2010, provisional application No. 61/376,194, filed on Aug. 23, 2010.

(51) Int. Cl.
| A61K 31/045 | (2006.01) |
| A61K 31/355 | (2006.01) |
| B82Y 5/00 | (2011.01) |
| A61K 9/14 | (2006.01) |
| A61K 9/51 | (2006.01) |

(52) U.S. Cl.
CPC .............. *A61K 31/045* (2013.01); *A61K 31/355* (2013.01); *B82Y 5/00* (2013.01); *A61K 9/14* (2013.01); *A61K 9/146* (2013.01); *A61K 9/5146* (2013.01)

(58) Field of Classification Search
CPC .......................... A61K 31/355; A61K 31/045
USPC ......................................................... 514/458
See application file for complete search history.

(56) References Cited

U.S. PATENT DOCUMENTS

| 5,278,189 | A | 1/1994 | Rath et al. |
| 7,214,394 | B2 | 5/2007 | Empie et al. |
| 7,320,802 | B2 | 1/2008 | Ryde et al. |
| 7,763,278 | B2 | 7/2010 | Cooper et al. |
| 2003/0054978 | A1* | 3/2003 | Babish ............................. 514/2 |
| 2003/0232796 | A1* | 12/2003 | Cooper et al. ................ 514/169 |
| 2005/0095297 | A1 | 5/2005 | Grenier et al. |
| 2005/0234025 | A1 | 10/2005 | Kutney et al. |
| 2005/0267091 | A1 | 12/2005 | Berlin |
| 2006/0020007 | A1 | 1/2006 | Berlin |
| 2006/0020043 | A1 | 1/2006 | Berlin |
| 2006/0148735 | A1 | 7/2006 | Rosenzweig et al. |
| 2007/0065497 | A1 | 3/2007 | Guilford |
| 2007/0281045 | A1 | 12/2007 | Tripp et al. |
| 2008/0107638 | A1 | 5/2008 | Treadwell |
| 2008/0206155 | A1 | 8/2008 | Tamarkin et al. |
| 2008/0207748 | A1 | 8/2008 | Perez |
| 2008/0227747 | A1 | 9/2008 | Tabbiner |
| 2010/0143962 | A1 | 6/2010 | Cooper et al. |

FOREIGN PATENT DOCUMENTS

| WO | WO 9636316 A1 | 11/1996 |
| WO | WO 0051572 A1 | 9/2000 |
| WO | WO 03013474 A1 | 2/2003 |
| WO | WO 2006039268 A2 | 4/2006 |
| WO | WO 2007092509 A2 | 8/2007 |
| WO | WO 2009120919 A2 | 10/2009 |
| WO | WO 2011043237 A1 | 4/2011 |

OTHER PUBLICATIONS

CAS Registry No. 142583-61-7. SciFinder. Accessed Jun. 9, 2013.*
Adler, et al., "Association of systolic blood pressure with macrovascular and microvascular complications of type 2 diabetes (UKPDS 36): prospective observational study" BMJ, 321:412-419 (Aug. 12, 2000).
Aggarwal, "Signaling pathways to the TNF superfamily: a double-edged sword" Nat Rev Immunol. , 3(9):745-56 (Sep. 2003).
Aradhya, et al., "NF-kappaB signaling and human disease", Curr Opin Genet Dev., 11(3):300-6, (2001).
Bawa, "Nanoparticle-based therapeutics in Humans: a survey" Nanotechnology Law & Business, 5(2):135-155 (Summer 2008).
Dullens, et al., "Effects of emulsified policosanols with different chain-lengths on cholesterol metabolism in heterozygous LDL-receptor deficient mice" Journal of Lipid Research, Downloaded Jan. 30, 2009.
Dupont, "Overview of the lipid formulations of amphotericin B" Journal of Antimicrobial Chemotherapy, 49(Suppl. S1):31-36 (2002).
Garuda International, Inc., "LesstanoL® Policosanol 60 (Polycosanol) Raw Material" Accessed from: http://www.garudaint.com/prodspec.php?prod_code=OCTA-60, May 2007.
Garuda International, Inc., "LesstanoL® Octacosanol 95" Accessed from: http//www.garudaint.com/prodspec_pdf.php?prod_code=OCTA-95, Sep. 2004.
Hans, et al., "Nanoparticles for Drug Delivery, Section 23.3.1" Department of Materials Science and Engineering, Drexel University, Philadelphia, PA, p. 8 (2006).
Ismael, et al., "Blockade of sensory abnormalities and kinin $B_1$ receptor expression by *N*-acetyl-$_L$-cysteine and ramipril in a rat model of insulin resistance" Eur J Pharmacol. 589:66-72 (2008).
Jain, "Hyperglycemia can cause membrane lipid peroxidation and osmotic fragility in human red blood cells", J. Biol Chem, 264(35):21340-21345 (1989).
Jain, et al., "Erythrocyte membrane lipid peroxidation and glycosylated hemoglobin in diabetes", Diabetes, 38(12):1539-43, (Dec. 1989).

(Continued)

*Primary Examiner* — Jeffrey S Lundgren
*Assistant Examiner* — Chris Simmons
(74) *Attorney, Agent, or Firm* — Morgan, Lewis & Bockius LLP

(57) ABSTRACT

The present invention provides nanoparticulate policosanol, and octacosanol formulations including these particles, as a well as methods of using the particles and formulations for treatment and prophylaxis of various diseases and conditions.

14 Claims, 31 Drawing Sheets

(56) References Cited

OTHER PUBLICATIONS

Kassis, "Evaluation of cholesterol-lowering and antioxidant properties of sugar cane policosanols in hamsters and humans", School of Dietetics and Human Nutrition, McGill University, Montreal, Canada: 1-226 (Apr. 2008)

Kumar, et al., "Nuclear factor-kappaB: its role in health and disease", J Mol Med 82(7):434-48 (Jul. 2004).

Levy, et al., "Corrective homeostasis model assessment (HOMA) evaluation uses computer program", Diabetes Care, 21(12):2191-2 (Dec. 1998).

Marinangeli, et al., "Policosanols as nutraceuticals: fact or fiction" Critical Reviews of Food Science and Nutrition, 50:259-267 (2010).

Meng, et al., "Akt is a downstream target of NF-kappaB", J. Biol Chem, 277(33):29674-29680 (Aug. 16, 2002).

Michael, et al., "Loss of Insulin Signaling in Hepatocytes Leads to Severe Insulin Resistance and Progressive Hepatic Dysfunction" Molecular Cell, 6:87-97 (2000).

Nishikimi, et al. "Molecular basis for the deficiency in humans of gulonolactone oxidase, a key enzyme for ascorbic acid biosynthesis", Am J Clin Nutr, 54:1203S-1208S (1991).

Shea, et al., "Nanosphere-mediated delivery of vitamin E increases its efficacy against oxidative stress resulting from exposure to amyloid beta" Journal of Alzheimer's Disease, 7:1-5 (2005).

Stratton, et al. "Association of glycaemia with macrovascular and microvascular complications of type 2 diabetes (UKPDS 35): prospective observational study" BMJ, 321: 412-419 (Aug. 12, 2000).

Yamamoto, et al., "Role of the NF-kappaB pathway in the pathogenesis of human disease states", Curr Mol Med. 1(3):287-96 (Jul. 2001).

Yan, et al., "Efficacy of hypochlorous acid scavengers in the prevention of protein carbonyl formation" Arch Biochem Biophys 327(2):330-334 (Mar. 15, 1996).

Yaturu, et al., "Resistin and adiponectin levels in subjects with coronary artery disease and type 2 diabetes", Cytokine, 34(3-4): 219-23 (May 2006).

Yerneni, et al., "Hyperglycemia-induced activation of nuclear transcription factor kappaB vascular smooth muscle cells", Diabetes, 48:855-64 (1999).

* cited by examiner

Glycated hemoglobin levels

POLICOSANOL NANOPARTICLES

CROSS-REFERENCE TO RELATED APPLICATION

This application claims priority to U.S. Provisional Application No. 61/376,194, filed Aug. 23, 2010, and No. 61/376,645, filed Aug. 24, 2010, the disclosures of which are incorporated herein by reference in their entirety for all purposes.

FIELD OF THE INVENTION

The present invention relates to nanoparticulate compositions comprising at least one policosanol, novel nanoparticulate policosanol formulations, and uses thereof. In various embodiments, the nanoparticulate policosanol particles have an effective average particle size of less than about 100 nm.

BACKGROUND OF THE INVENTION

Policosanol is a complex mixture of concentrated long chain N-alkyl alcohols derived from plant sources, such as sugar cane. Octacosanol is a major constituent of naturally derived policosanol, e.g. from sugarcane. Much of the published work on policosanol has been directed to mixtures in which octacosanol was a major component. Early work in Cuba studying the effects of policosanol on serum lipid and lipoprotein levels in healthy volunteers indicated that, at dosages of 2-40 mg/d, policosanol administration reduced serum lipid and lipoprotein levels (Hernandez et al., *Curr. Ther. Res. Clin. Exp.* 1992; 51: 568), and reduced hypercholesterolemia (Pons et al., *Curr. Ther. Res. Clin. Exp.;* 1992; 52: 507). However, despite numerous subsequent studies, researchers outside Cuba have been unable to verify the claims made in conjunction with the original research. The ineffectiveness of policosanol on serum lipid/cholesterol levels has been comprehensively documented in respected, peer-reviewed journals.

For example, Francini-Pesenti and coworkers conducted double blinded, randomized, placebo-controlled trials of policosanol in subjects with hypercholesterolemia and concluded that doses of 10 mg/d and 20 mg/d of policosanol showed no lipid lowering effects (*Complement Ther. Med.;* 2008; 16(2): 61; and *Phytother. Res.;* 2008; 22(3): 318). In a similar blind, placebo-controlled study, Berthold and coworkers showed that doses of 10, 20, 40 and 80 mg/d of policosanol did not result in lower serum lipid levels than those seen in subjects to whom the placebo was administered (*JAMA;* 2006; 295(19): 2262). Dullens et al. found that neither individual policosanol components (C24, C26, C28, or C30) nor the natural policosanol mixture (all components, 30 mg/100 g diet) lowered serum cholesterol concentrations in LDL receptor knockout mice (*J. Lipid Res.;* 2008; 49(4): 790). Kassis and coworkers studied the efficacy of Cuban sugar cane policosanols for treating hypercholesterolemia in humans at a dosage of 10 mg/d and concluded that policosanol had no beneficial effects on lipid indicators in hypercholesterolemia subjects (*Am. J. Clin. Nutr;* 2006; 84(5): 1003). Lin and coworkers studied the effects of 20 mg/d dosages of wheat germ policosanol in subjects with normal to mildly elevated plasma cholesterol and detected no lowering of plasma cholesterol (*Metabolism;* 2004; 53(10): 1309). Lukashevich et al. found that beeswax policosanol (10 mg or 40 mg) administered daily in tablet or soft gel formulations had no effect on serum lipids in subjects with mild-to-moderate hypercholesterolemia. (*Circulation;* 2006; 114: 892). Murphy et al. found dietary supplementation of rabbits with policosanol from sunflower oil did not have any cholesterol lowering effect. (*J. Am. College Nutr;* 2008; 27(4): 476).

Thus, despite the early apparently promising results of the Cuban research, the conclusion that must be reached from contemporary blinded, placebo-controlled studies is that art-recognized policosanol formulations are not effective at modulating serum lipid/cholesterol levels.

Research on the utility of policosanol formulations on other metabolic and physiologic parameters has produced similarly negative results. For example, policosanol was shown to have no effect on blood sugar levels, glycemic control (Crespo et al., *Int. J. Clin. Pharm. Res.;* 1999: 117) or diabetic status (Shinbori et al., *Eur. J. Pharmacol;* 2007; 139-144).

A controversy existed for a time regarding whether the composition or formulation of the policosanol used in the Cuban studies was responsible for the inconsistent results between the Cuban research and that of other workers. This controversy has been put to rest in seminal research. (Kassis, *British Journal of Nutrition* (2007), 97, 381-388; Kassis, *Lipids Health Dis.* (2008); 7:17; Kassis *Appl. Physiol. Nutr. Metab*; (2008); 33(3): 540 and Dullens *J. Lipid Res.* (2008), 49: 790). They studied utilized different sugar cane derived policosanol formulations, including the formulation used in the Cuban research. Their studies concluded that none of the tested policosanol formulations significantly improved lipid parameters in humans or animals relative to the control. Moreover, the in vivo assessment of LDL oxidation showed no significant alteration in oxidized LDL concentration relative to the baseline and control. Thus, as of mid-2008, the controversy regarding the serum lipid lowering effects of the Cuban as well as other sugar cane policosanol formulations is resolved outside Cuba.

There are very few reports in the literature on the therapeutic effects of pure octacosanol. Kim et. al., (Journal of Medicinal Food. (December 2003), 6(4): 345-351) evaluated the effects of octacosanol on running performance and related biochemical parameters in exercise-trained rats run to exhaustion on a treadmill. Their results suggest that the ergogenic properties of octacosanol include the sparing of muscle glycogen stores and increasing the oxidative capacity in the muscle of exercise-trained rats. Ping-ping Zuo et. al., (*Acta Pharmacologica Sinica* (July 2010) 31, 765-774) on their rat studies suggested that octacosanol may be a promising agent for treatment of Parkinson's disease. Fallat R J, et. al., (Neurology 1986; 36:1263-1264) found that administration of octacosanol in patients with amyotrophic lateral sclerosis in a double-blind, placebo-controlled, crossover study did not show any benefits to neurologic and pulmonary function. In Jahreis G. (Lipids 2008; 43 (2): 109-15), octacosanol administration to humans decreases neutral sterol and bile acid concentration in feces but serum cholesterol levels were not influenced. S. Kato, et. al., (British Journal of Nutrition (1995), 73:433-441) fed a high-fat diet rats with octacosanol at very high dose of 10 gm/kilo and found that lipid absorption was not affected by the inclusion of octacosanol. Thippeswamy (Eur J Pharmacol 2008; 588 (2-3): 141-50) found that octacosanol inhibits angiogenesis. It is known that angiogenesis is involved in tumor growth and metastasis. Plat et. al (Journal of Lipid Research, Vol. 49, 790-796, April 2008) studied emulsified and finely dispersed policosanol constituents individually and came to the conclusion that the evaluated individual policosanols as well as the natural policosanol mixtures have no potential in reducing CHD risk through effects on serum lipoprotein concentrations.

SUMMARY OF THE INVENTION

The present invention provides nanoparticles and nanoparticulate formulations of policosanol as well as methods for making these nanoparticles and formulations. Quite surprisingly, the policosanol formulations of the invention lower cholesterol and serum lipids and reduce systolic and diastolic blood pressure. Moreover, the formulations of the invention exert antioxidant effects, mitigate insulin resistance and its consequences, and raise vitamin C levels. Accordingly, the invention also provides methods of treating disease and regulating metabolism by administering to a subject a formulation of the invention. The invention also provides methods of regulating metabolism and treating hypertension, hypercholesterolemia as well as several other diseases. For example, the for mutation of the invention is of use in controlling in vivo protein oxidation, regulating blood glucose levels, and can be used to treat and prevent insulin resistance and its consequences, e.g., diabetes, and the deleterious downstream effects thereof. Moreover, the formulations of the invention are of use in regulating in vivo vitamin C levels in a subject.

2. Octacosanol

The present invention provides nanoparticles and nanoparticulate formulations of octacosanol as well as methods for making these nanoparticles and formulations. Quite surprisingly, the octacosanol formulations of the invention lower cholesterol and serum lipids and blood glucose levels. Moreover, the formulations mitigate insulin resistance and its consequences. Accordingly, the invention also provides methods of treating disease and regulating metabolism by administering to a subject a formulation of the invention. The invention also provides methods of regulating metabolism and treating hypertension, hypercholesterolemia as well as several other diseases. For example, the formulation of the invention is of use in, regulating blood glucose levels, and can be used to treat and prevent insulin resistance and its consequences, e.g., diabetes, and the deleterious downstream effects thereof. Moreover, the formulations of the invention are of use in regulating in vivo the levels of VEGF (Vascular Endothelial Growth Factor) in diseases such as coronary artery disease, stroke, and chronic wounds. It can be used to deliver angiogenic growth factors to the heart, limbs, and wounds in a subject.

Thus, in various embodiments, the invention provides a nanoparticle of policosanol. A representative nanoparticle of the invention includes a policosanol fraction comprising about 60% to about 95%, e.g., from about 50% to about 69% octacosanol; and a stabilizer fraction. In an exemplary embodiment, the stabilizer fraction includes a poly (ethylene glycol) ester. In various embodiments, the stabilizer fraction includes a tocopheryl ester. Exemplary components of the stabilizer fraction include tocopheryl poly(ethylene glycol) esters, e.g., tocopheryl polyethylene glycol (1000) succinate ("TPGS"). Exemplary nanoparticles of the invention have a diameter of less than about 100 nm.

Thus, in various embodiments, the invention provides a nanoparticle of octacosanol. A representative nanoparticle of the invention includes a policosanol fraction comprising about 95% to about 100%, e.g., from about 95% to about 100% octacosanol; and a stabilizer fraction. In an exemplary embodiment, the stabilizer fraction includes a poly (ethylene glycol) ester. In various embodiments, the stabilizer fraction includes a tocopheryl ester. Exemplary components of the stabilizer fraction include tocopheryl poly(ethylene glycol) esters, e.g., tocopheryl polyethylene glycol (1000) succinate ("TPGS"). Exemplary nanoparticles of the invention have a diameter of less than about 100 nm Other objects, advantages, and embodiments of the invention are set forth in the detailed description that follows.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended Figures. These Figures form a part of the specification. It is to be noted, however, that the appended Figures illustrate preferred embodiments of the invention and therefore are not to be considered limiting in their scope.

DETAILED DESCRIPTION OF THE INVENTION AND THE

Preferred Embodiments

Definitions

Figure 1:
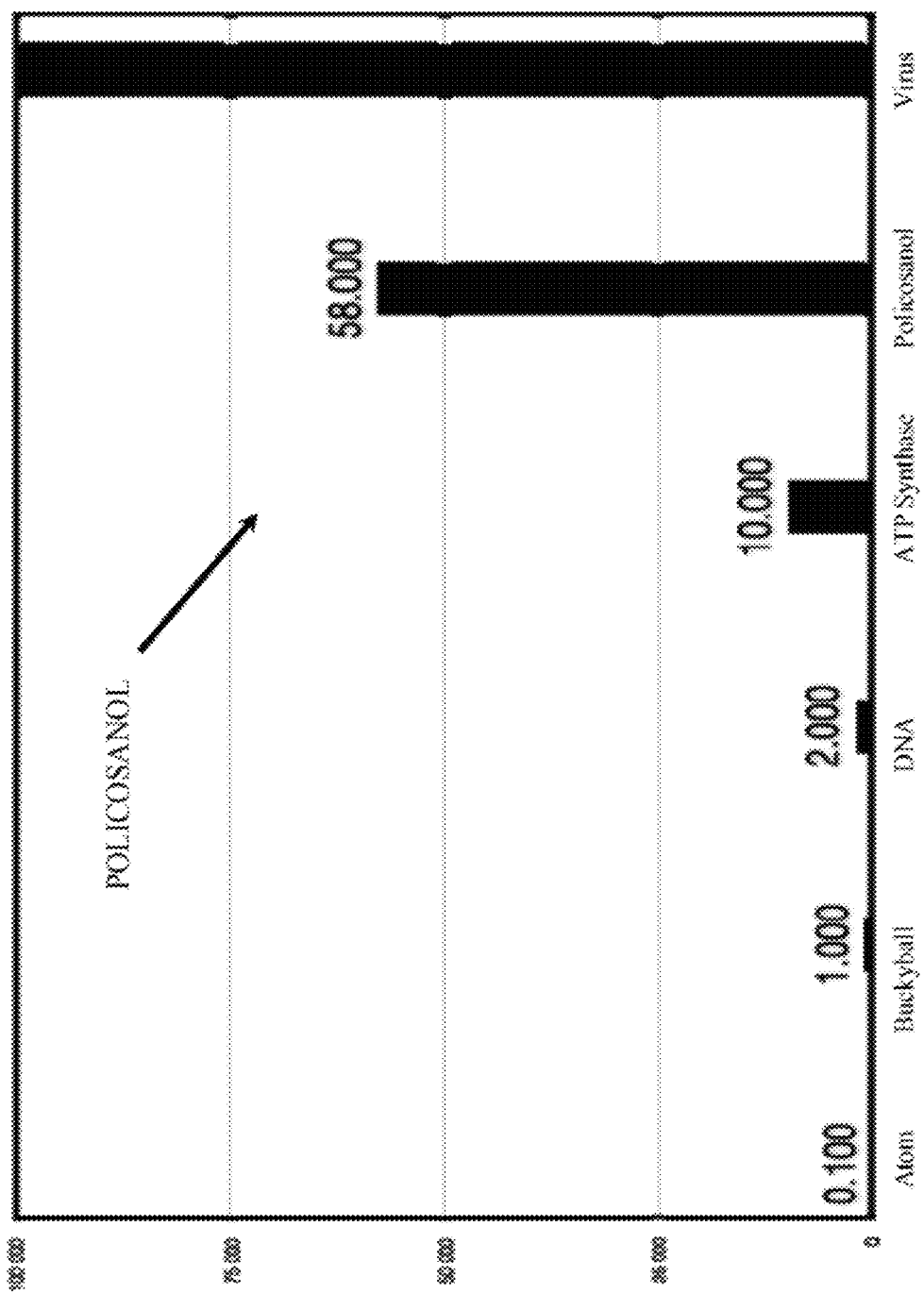
FIG. 1 shows the size of the size of the particles of the invention relative to other nanoparticles.
Figure 2:
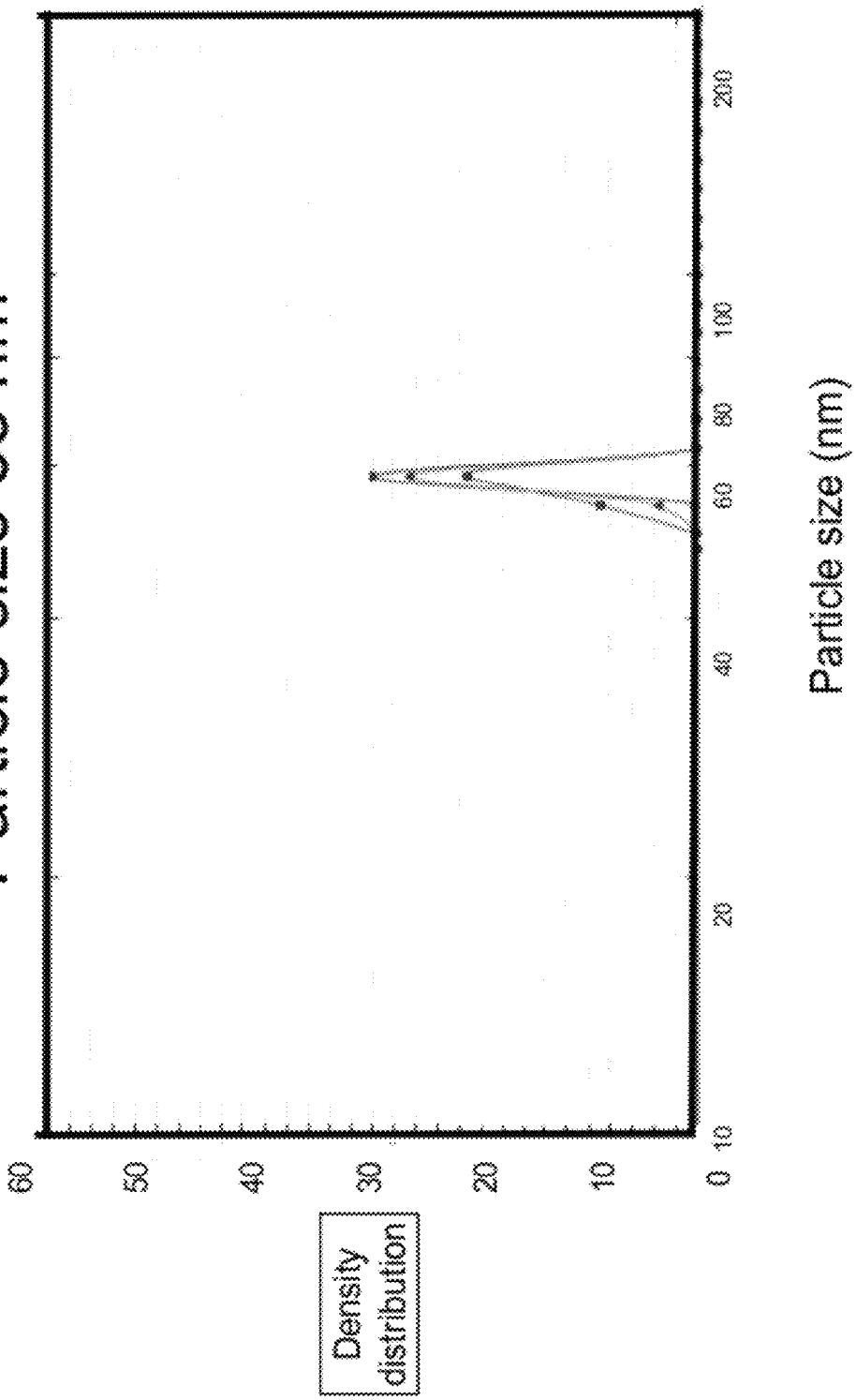
FIG. 2 shows the size distribution of nanoparticles of the invention with a peak at about 58 nm as measured by light scattering.
Figure 3:
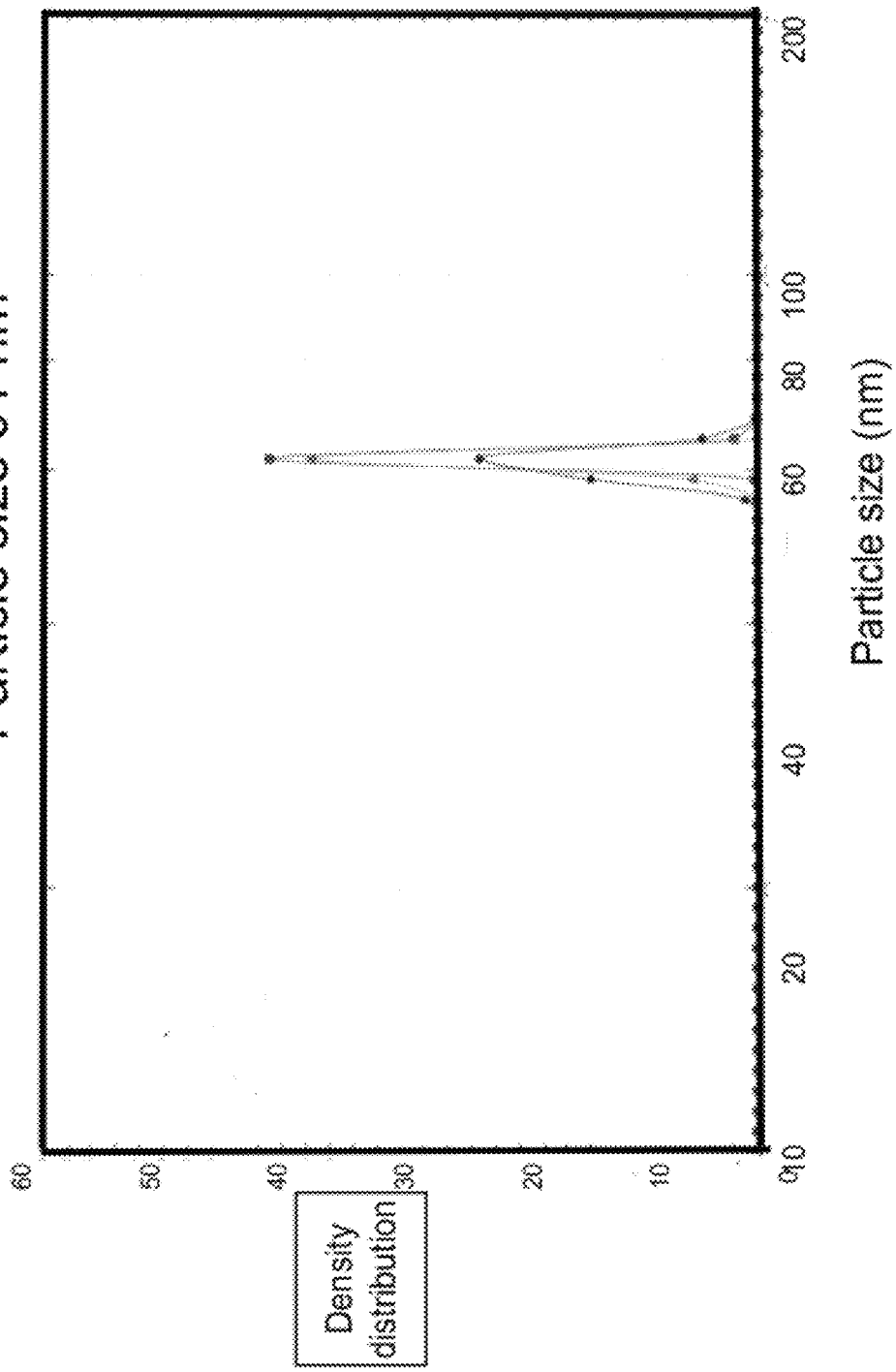
FIG. 3 shows the size distribution of nanoparticles of the invention with a peak at about 61 nm as measured by light scattering.
Figure 4:
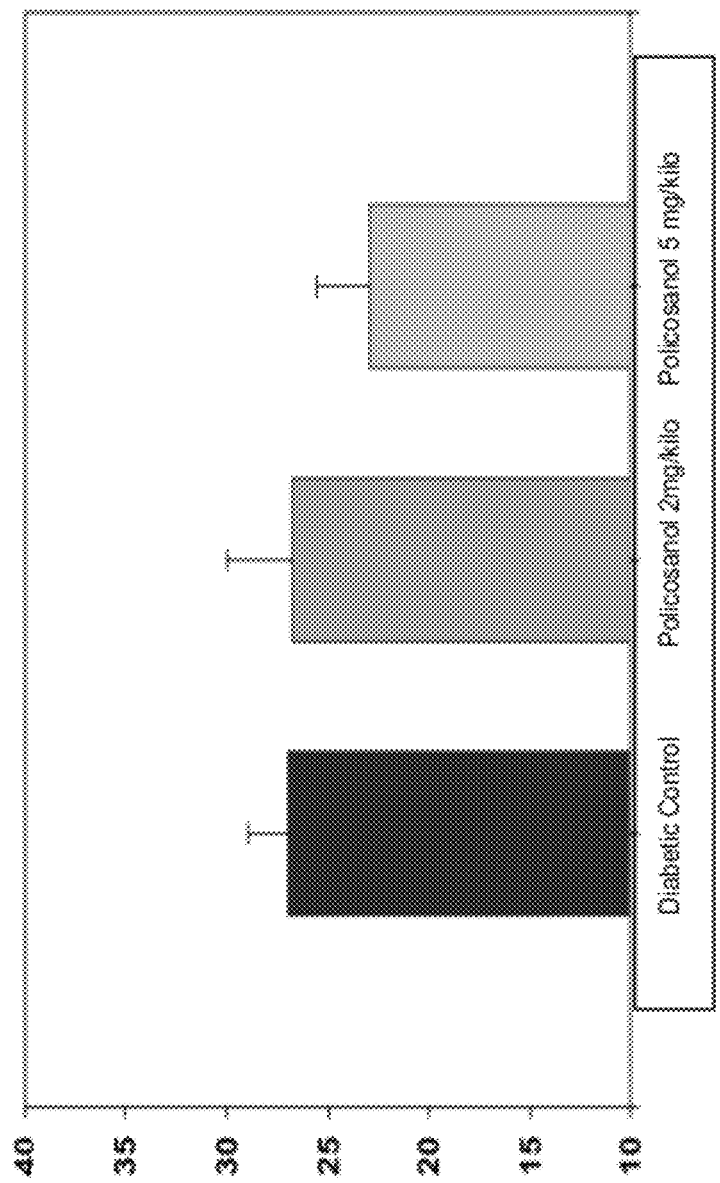
FIG. 4 shows levels of insulin resistance in untreated rats and rats treated with particles of the invention at 2 mg/kg and 5 mg/kg.
Figure 5:
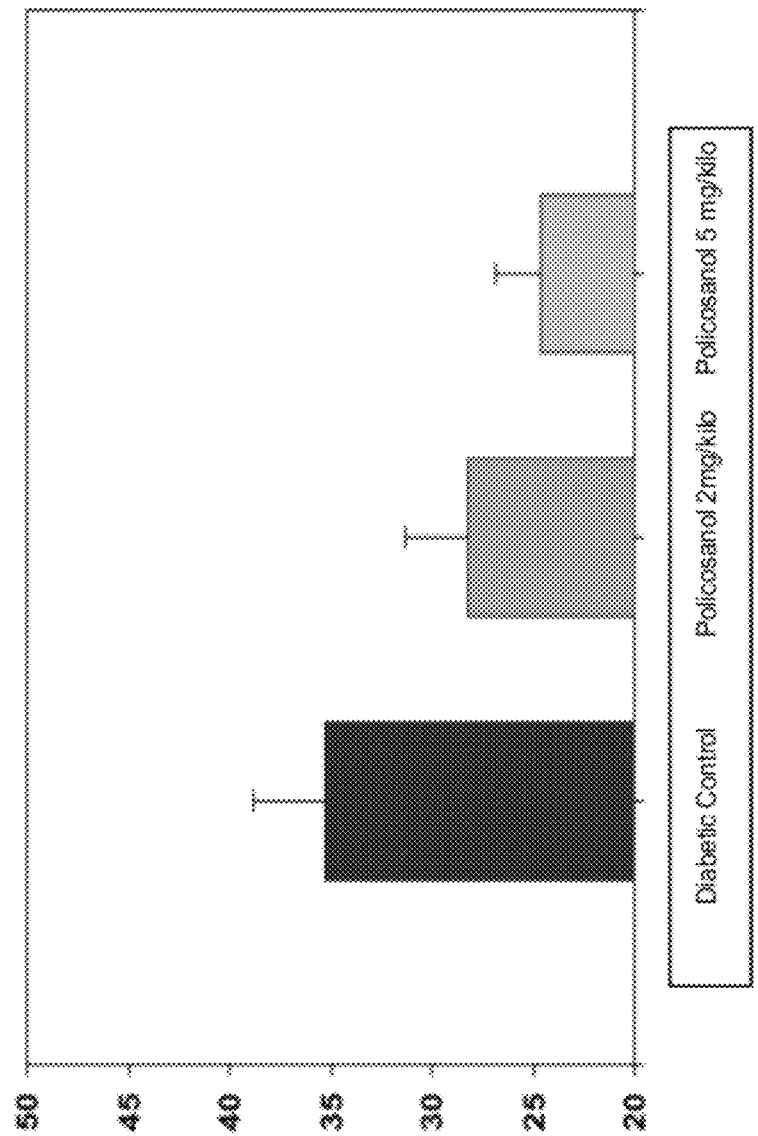
FIG. 5 shows fasting plasma levels of insulin in untreated rats and rats treated with particles of the invention.
Figure 6:
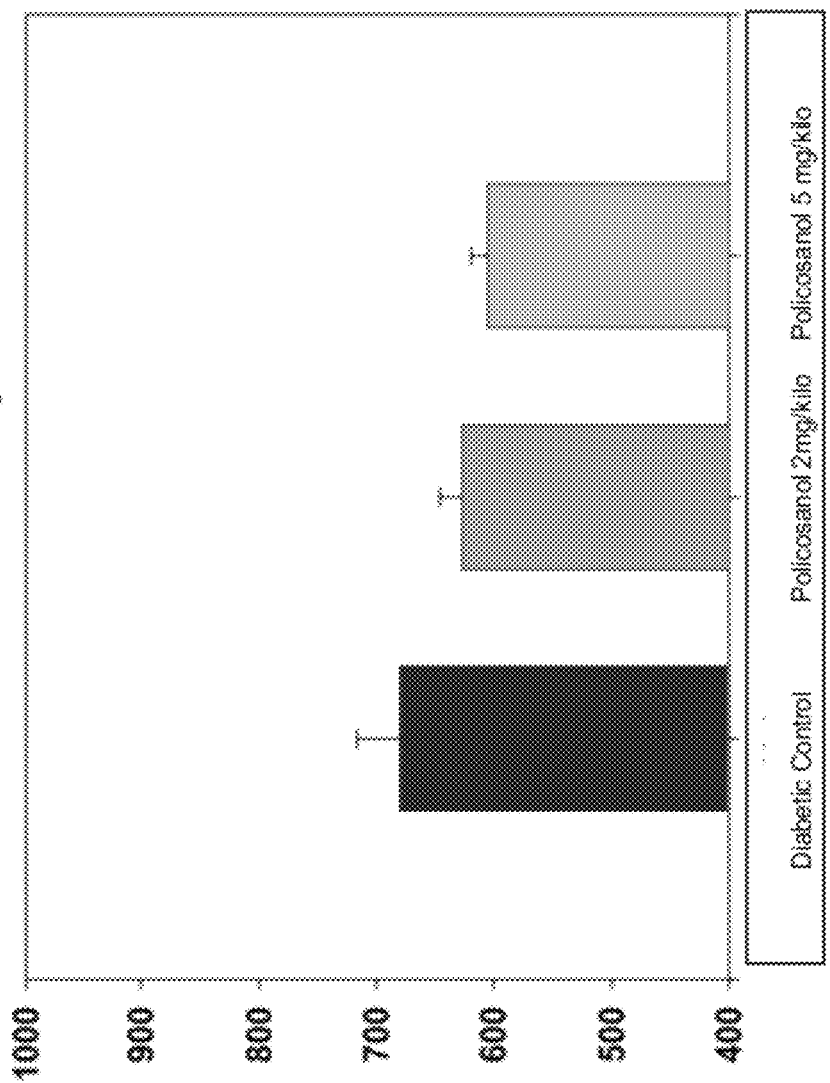
FIG. 6 shows levels of total cholesterol/HDL ratio in untreated rats and rats treated with particles of the invention at 2 mg/kg and 5 mg/kg.
Figure 7:
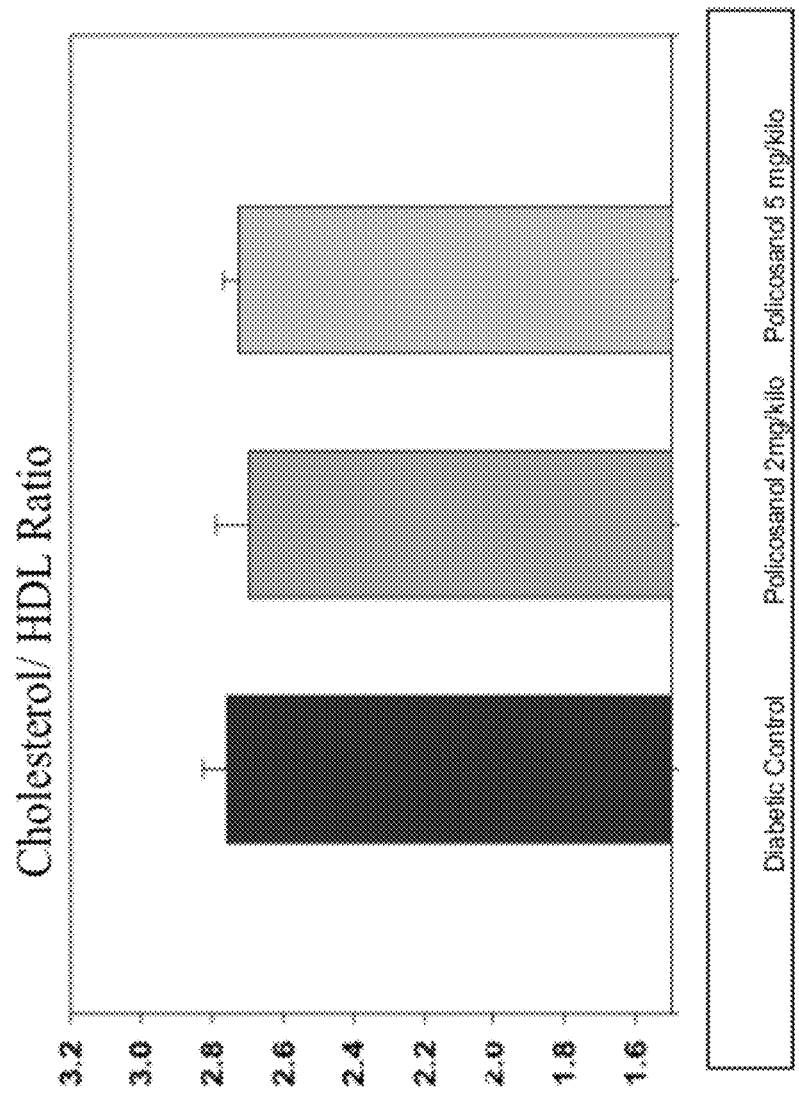
FIG. 7 shows blood levels of C-reactive protein in untreated rats and rats treated with particles of the invention at 1 mg/kg and 2 mg/kg.
Figure 8:
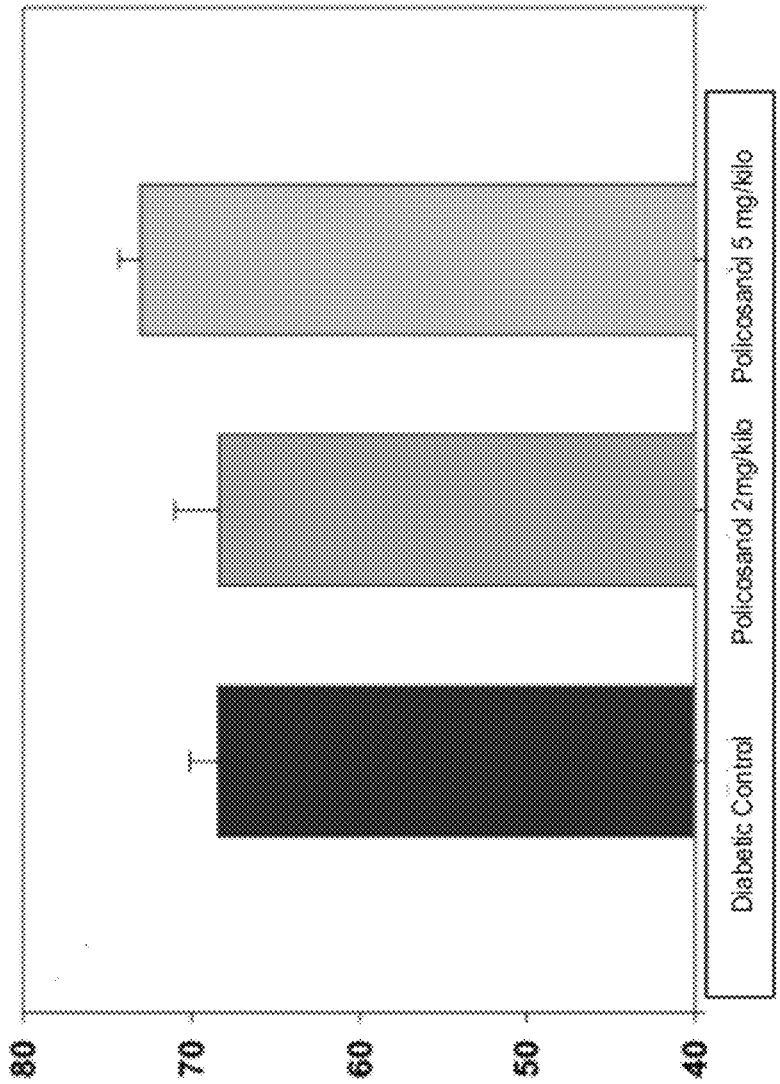
FIG. 8 shows levels of glycosylated hemoglobin (HbAlc) levels in untreated rats and rats treated with particles of the invention at 2 mg/kg and 5 mg/kg.
Figure 9:
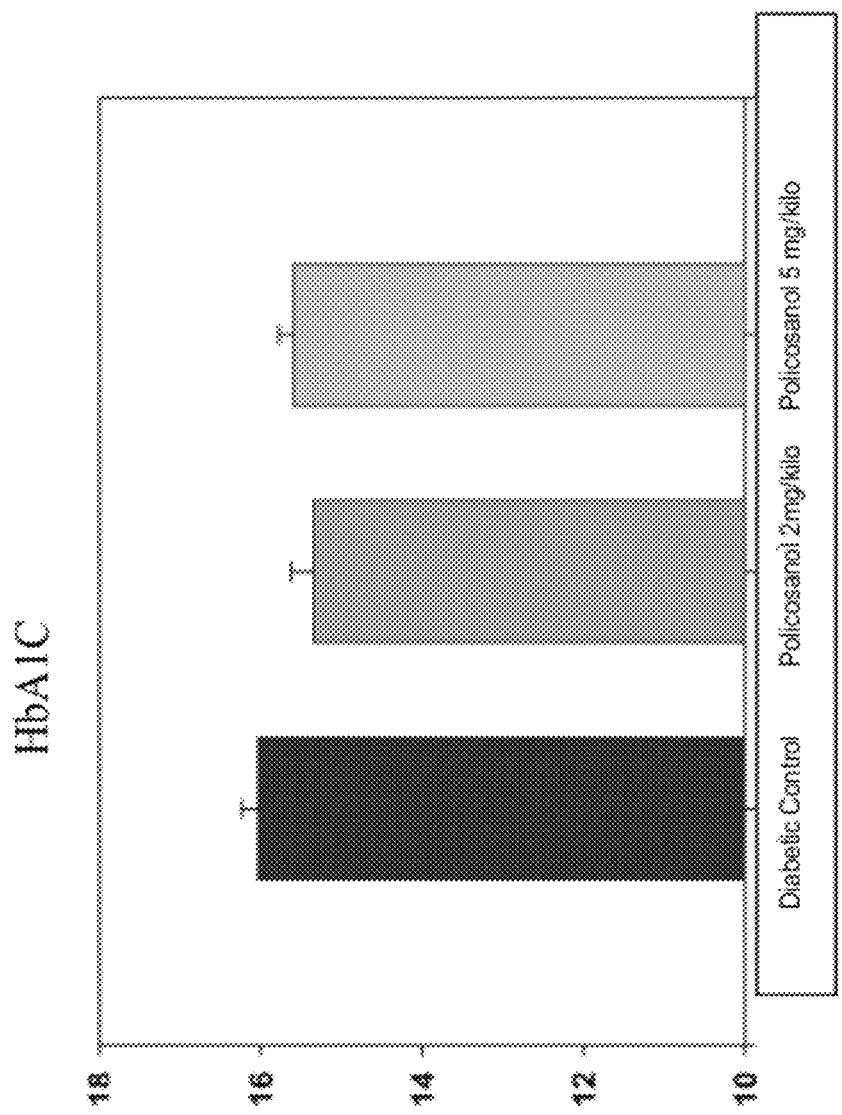
FIG. 9 shows HDL levels in untreated rats and rats treated with particles of the invention at 2 mg/kg and 5 mg/kg.
Figure 10:
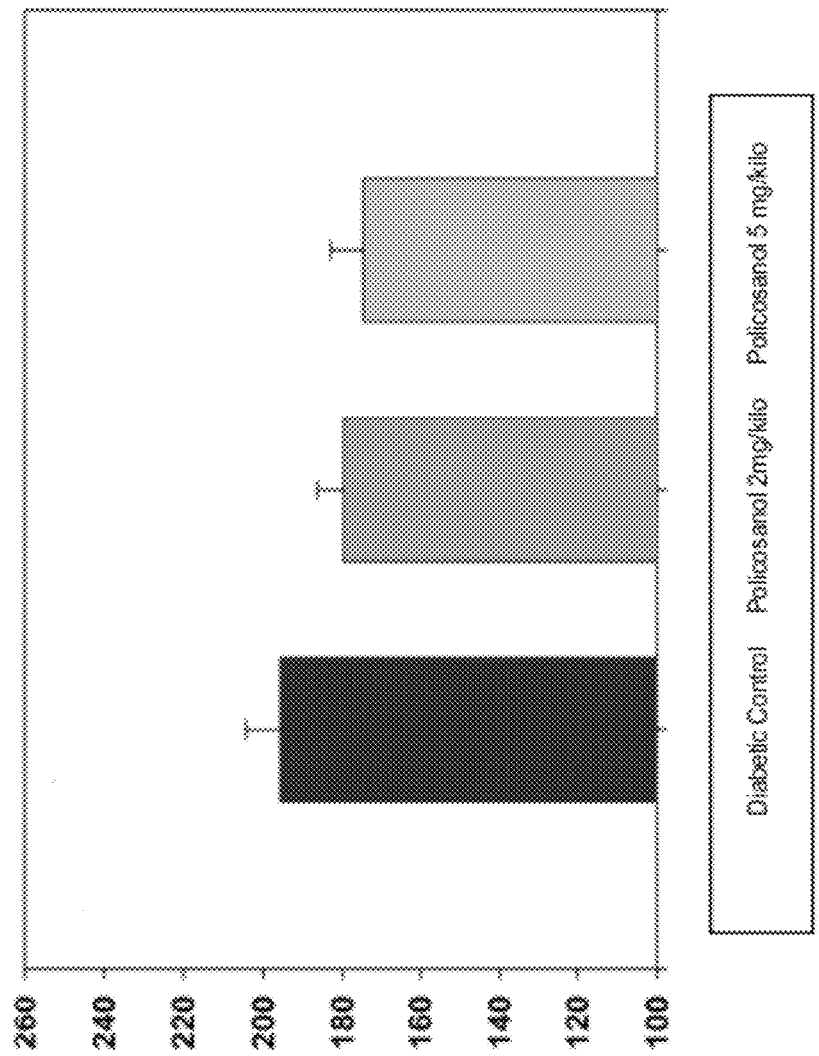
FIG. 10 shows the ICAM-1 (inter cellular adhesion molecule) levels in untreated rats and rats treated with particles of the invention at 2 mg/kg and 5 mg/kg.
Figure 11:
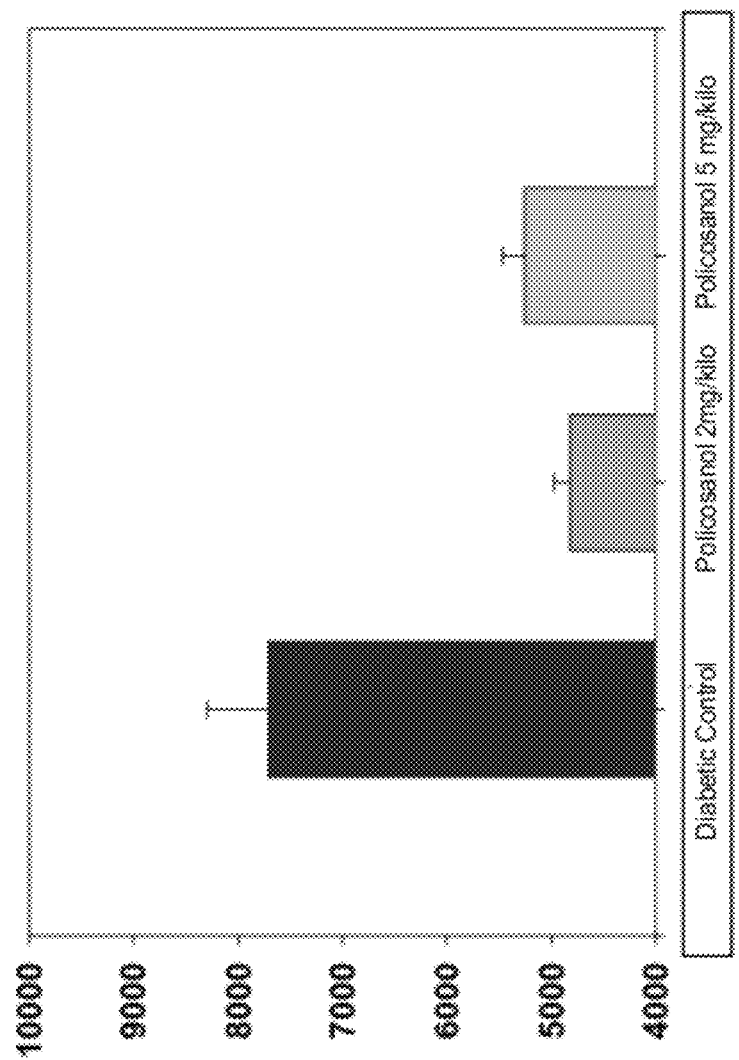
FIG. 11 shows MCP-1 (monocyte chemotactic protein-1) levels in untreated rats and rats treated with particles of the invention at 2 mg/kg and 5 mg/kg.
Figure 12:
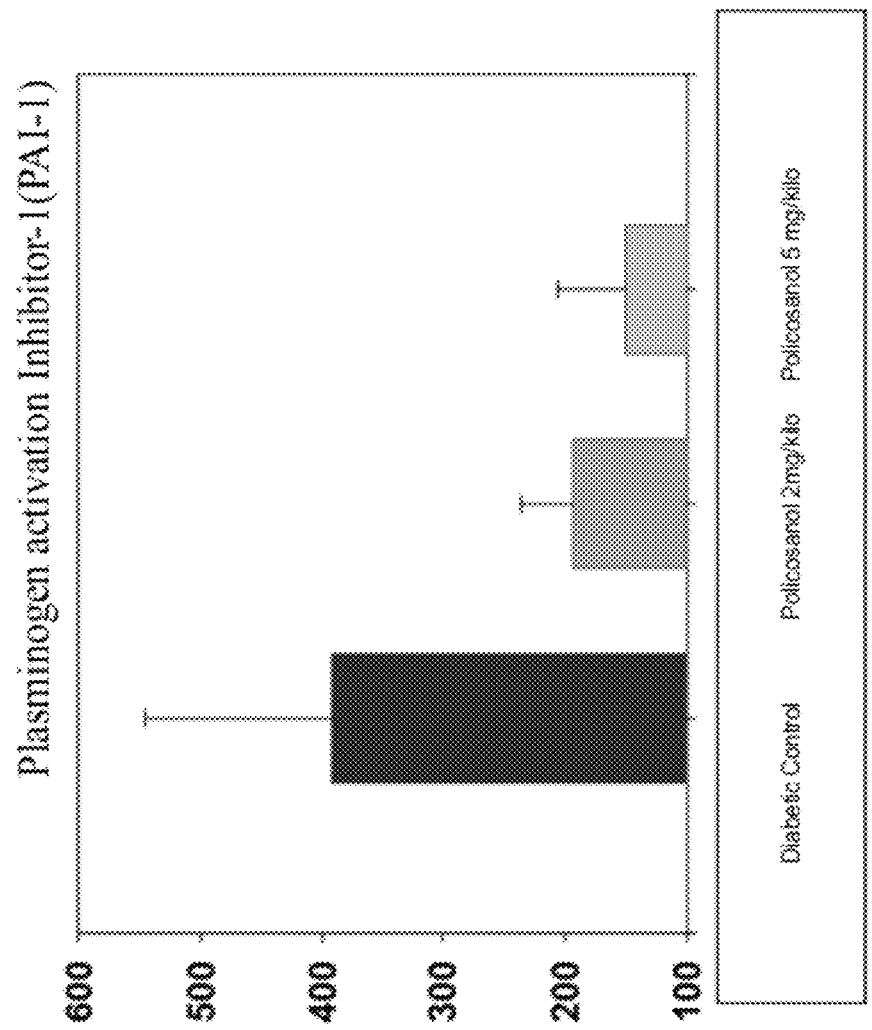
FIG. 12 shows PAI-1 (plasminogen activation inhibitor) levels in untreated rats and rats treated with particles of the invention at 2 mg/kg and 5 mg/kg.
Figure 13:
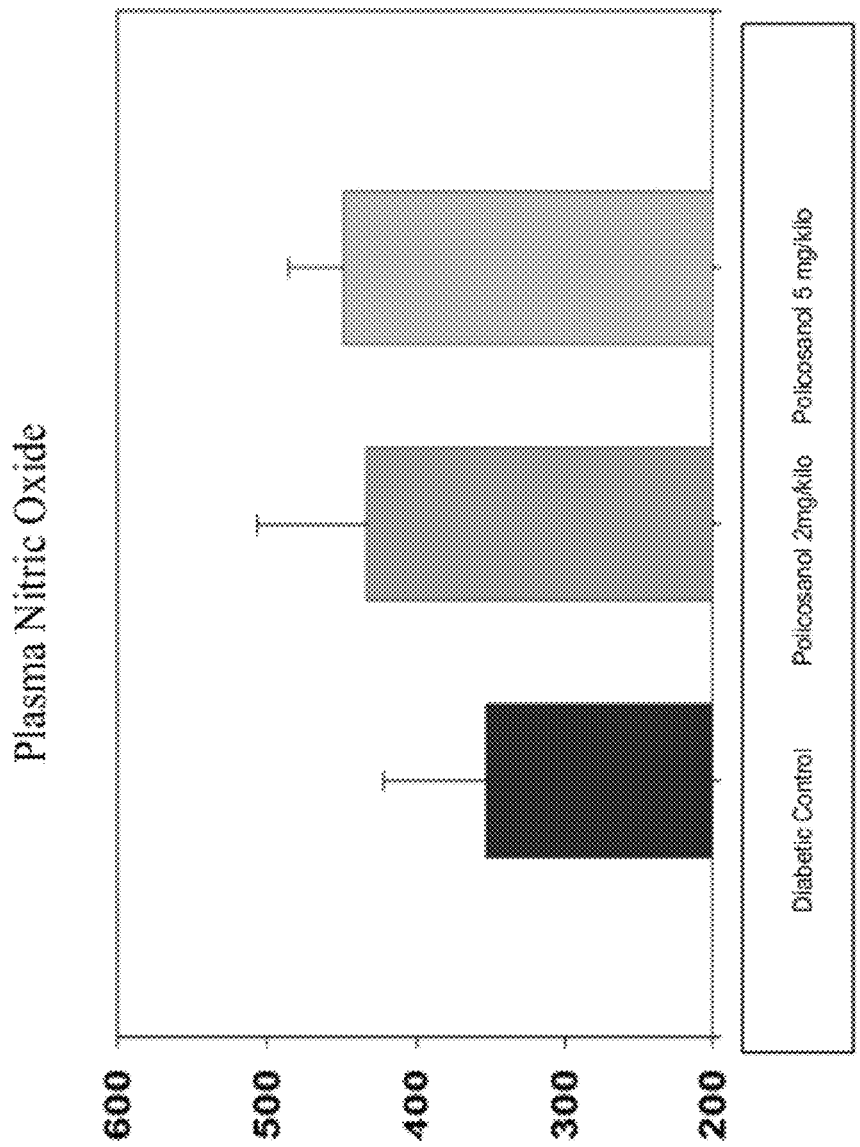
FIG. 13 shows nitric oxide levels in untreated rats and rats treated with particles of the invention at 2 mg/kg and 5 mg/kg.
Figure 14:
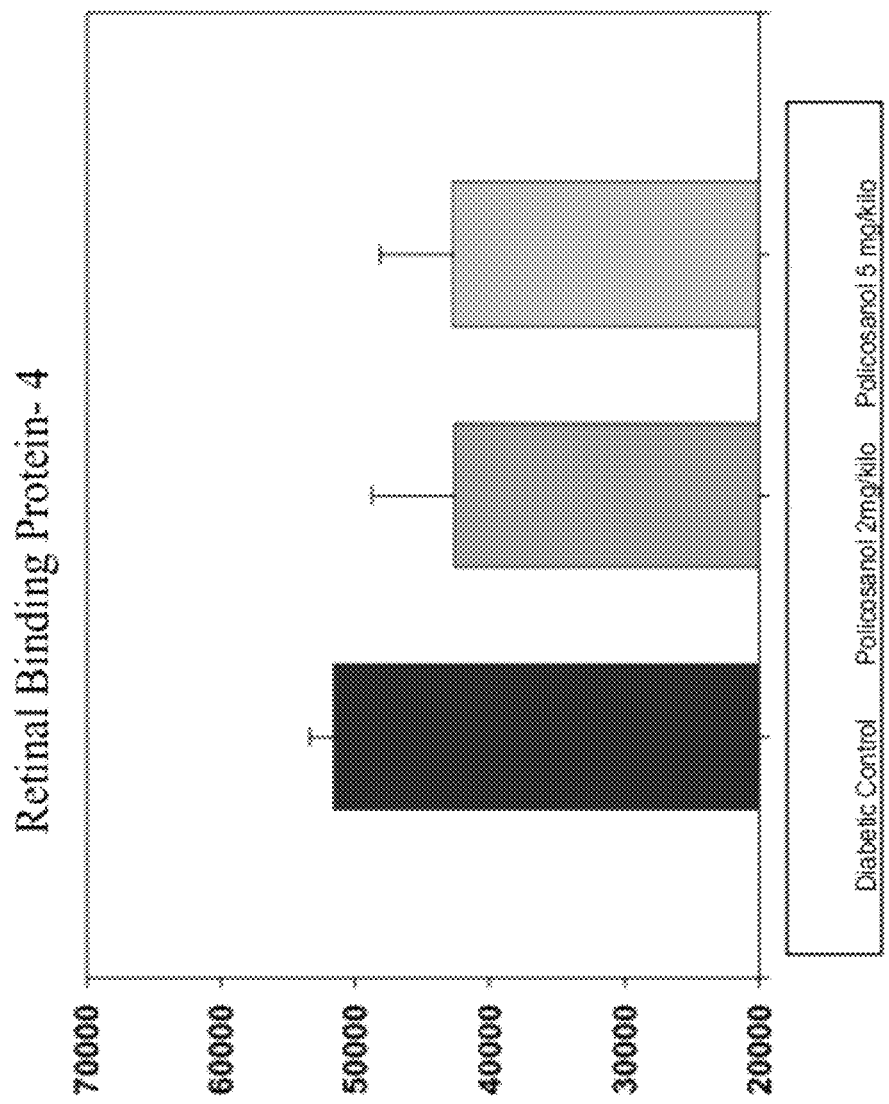
FIG. 14 shows protein oxidation levels in untreated rats and rats treated with particles of the invention at 2 mg/kg and 5 mg/kg.
Figure 15:
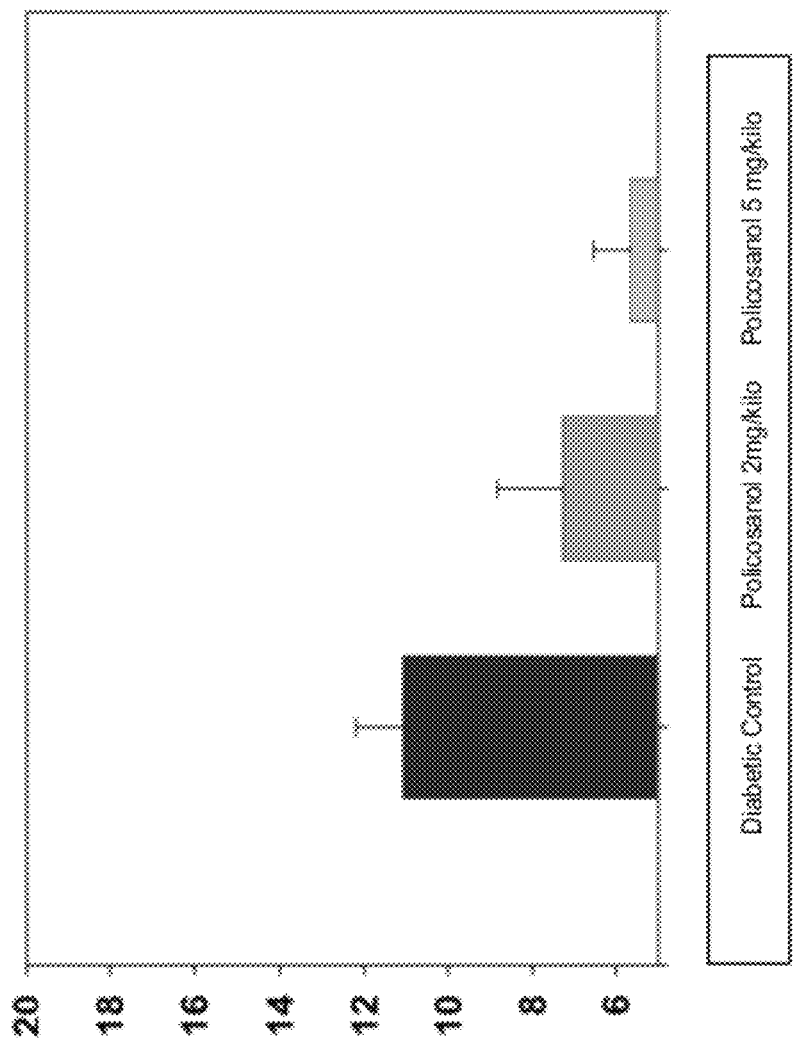
FIG. 15 shows RBP-4 (retinal binding protein) levels in untreated rats and rats treated with particles of the invention at 2 mg/kg and 5 mg/kg.
Figure 16:
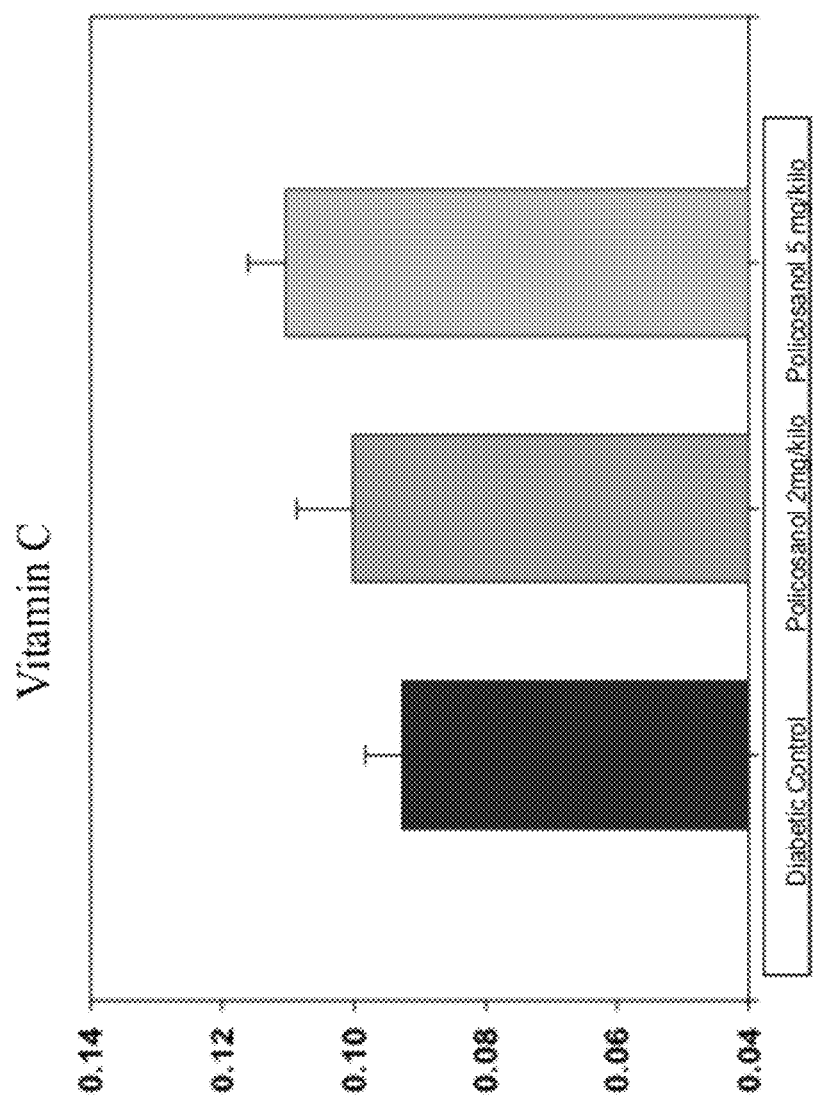
FIG. 16 shows vitamin-C levels in untreated rats and rats treated with particles of the invention at 2 mg/kg and 5 mg/kg.
Figure 17:
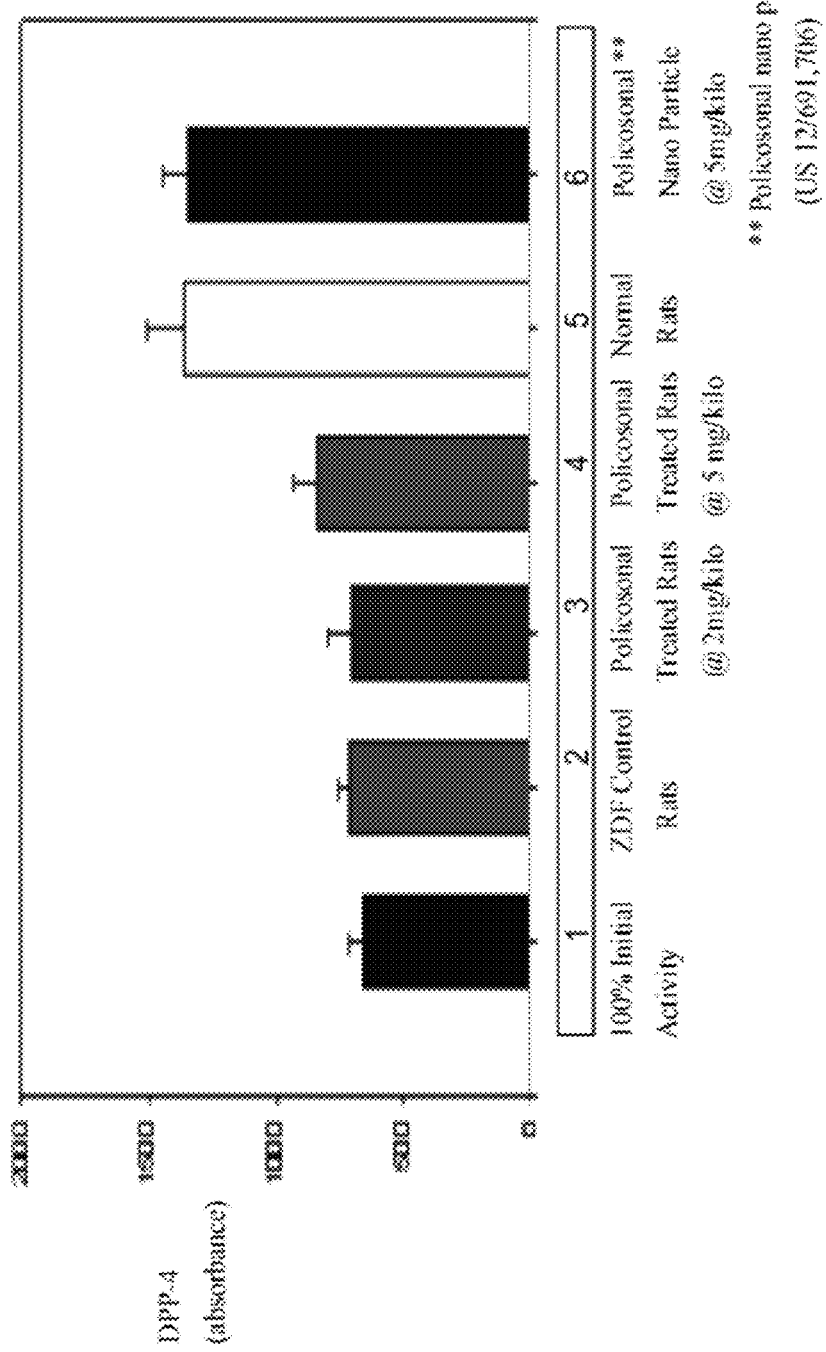
FIG. 17 shows levels of absorbance of DPP-IV assay in untreated rats and rats treated with particles of invention.
Figure 18:
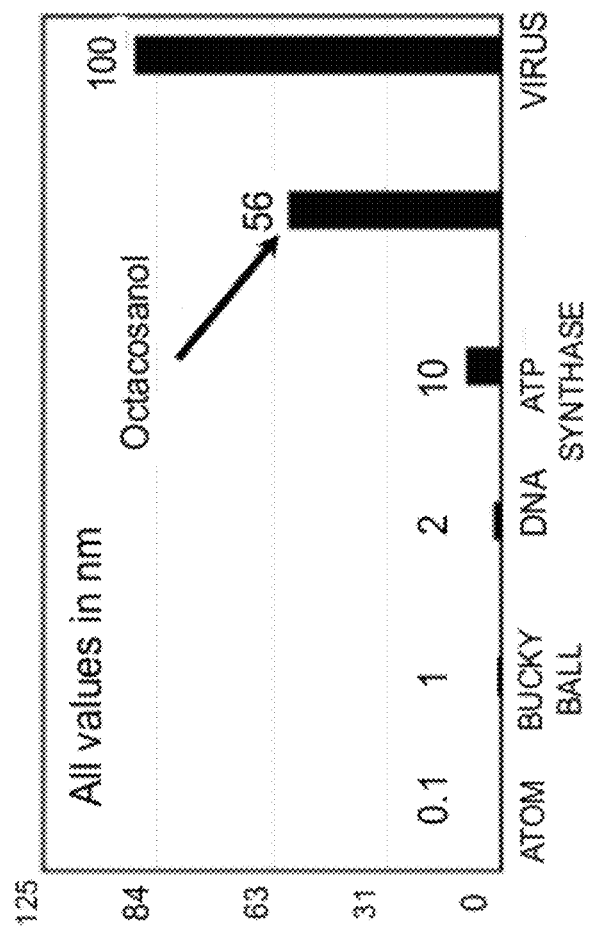
FIG. 18 shows the size of the particles of the invention relative to other nanoparticles.
Figure 19:
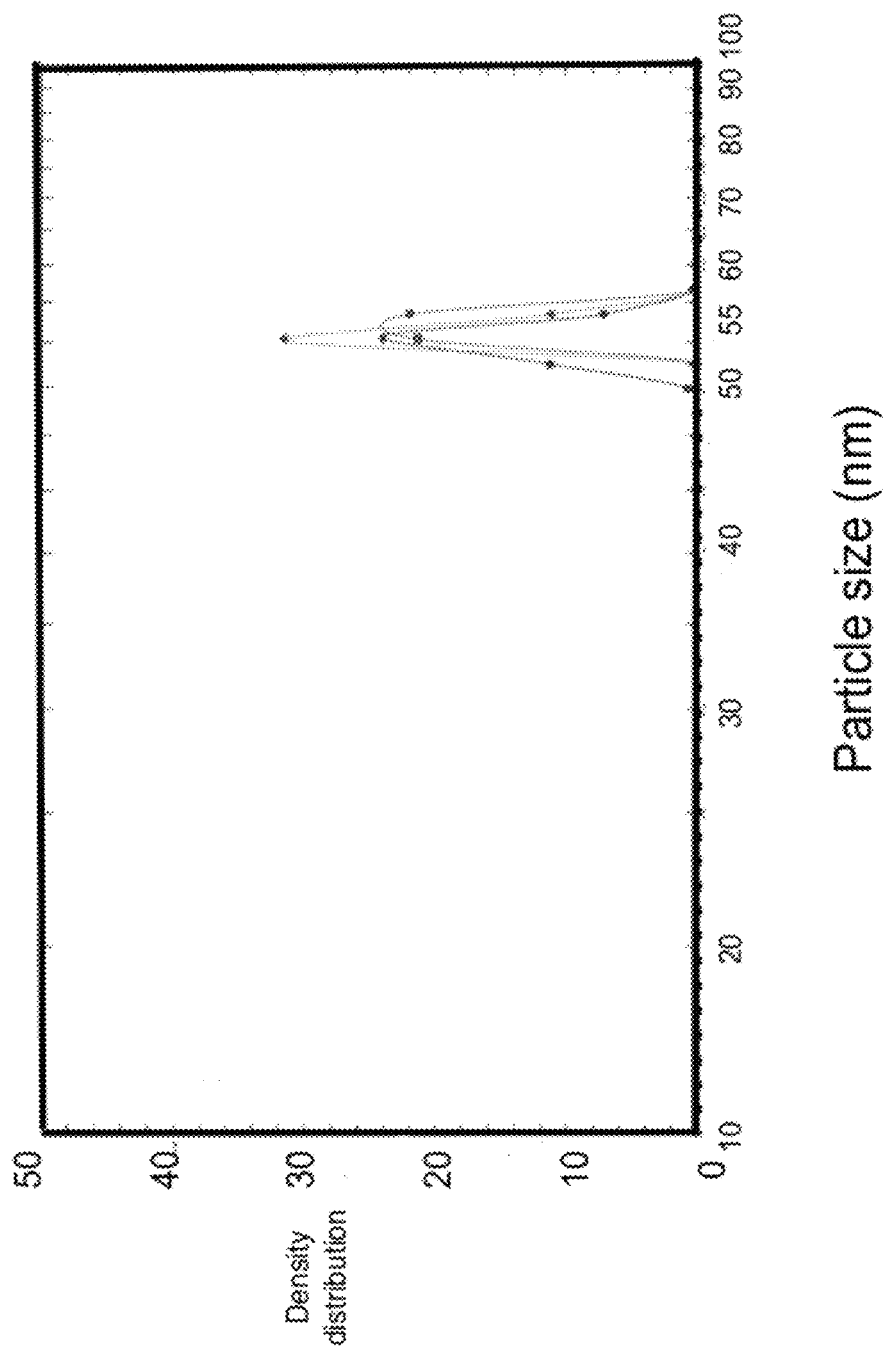
FIG. 19 shows the size distribution of nanoparticles of the invention with a peak at about 57 nm as measured by light scattering.
Figure 20:
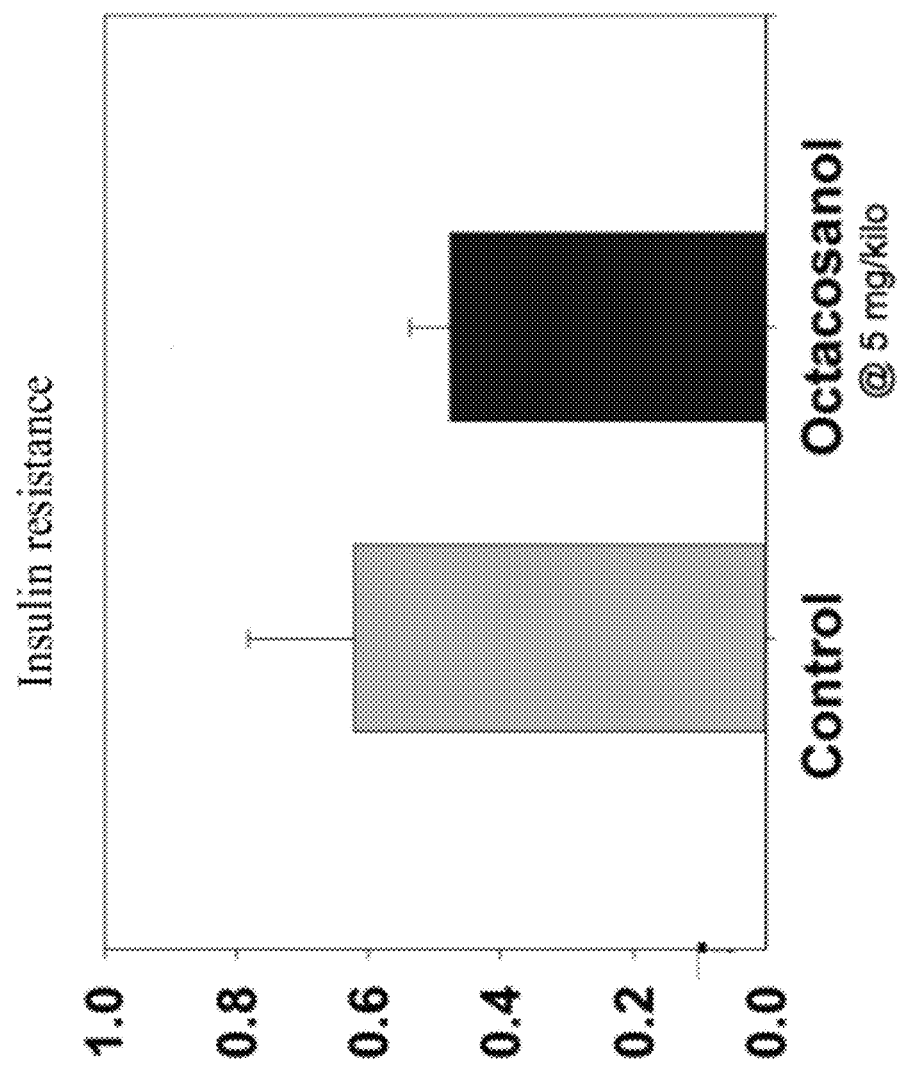
FIG. 20 shows levels of insulin resistance in untreated rats and rats treated with particles of the invention at 5 mg/kg.
Figure 21:
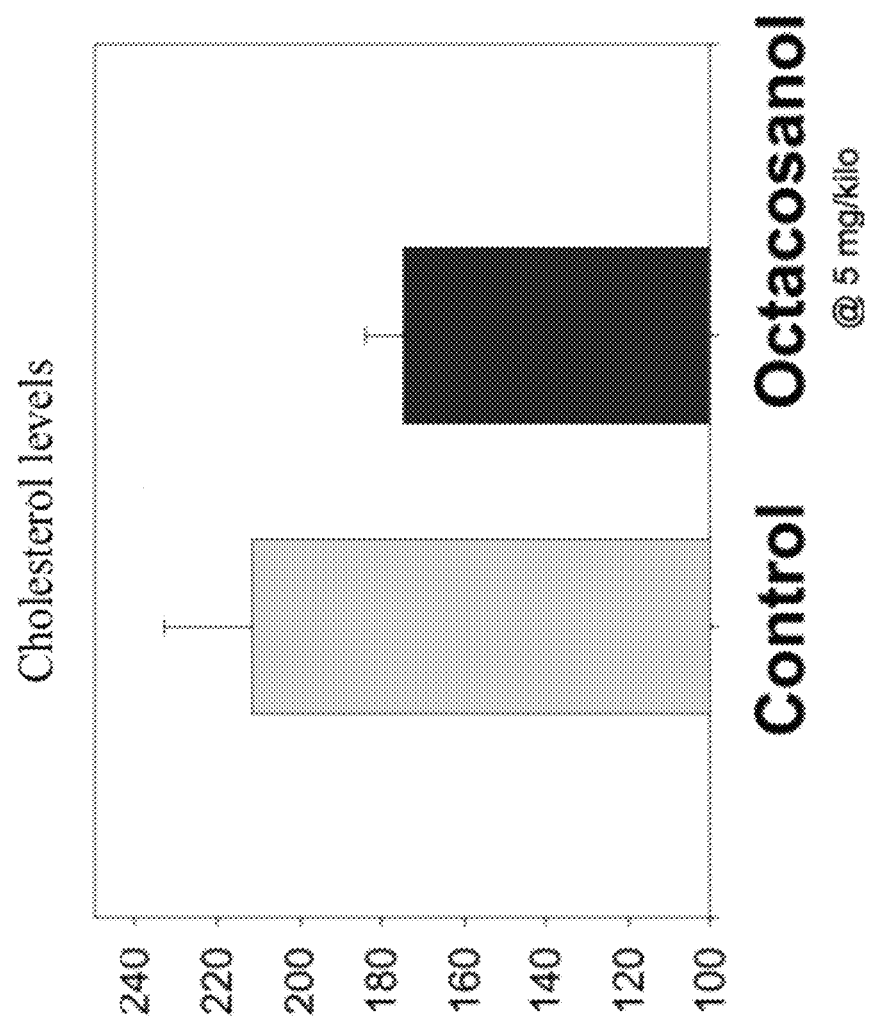
FIG. 21 shows cholesterol levels in untreated rats and rats treated with particles of the invention at 5 mg/kg.
Figure 22:
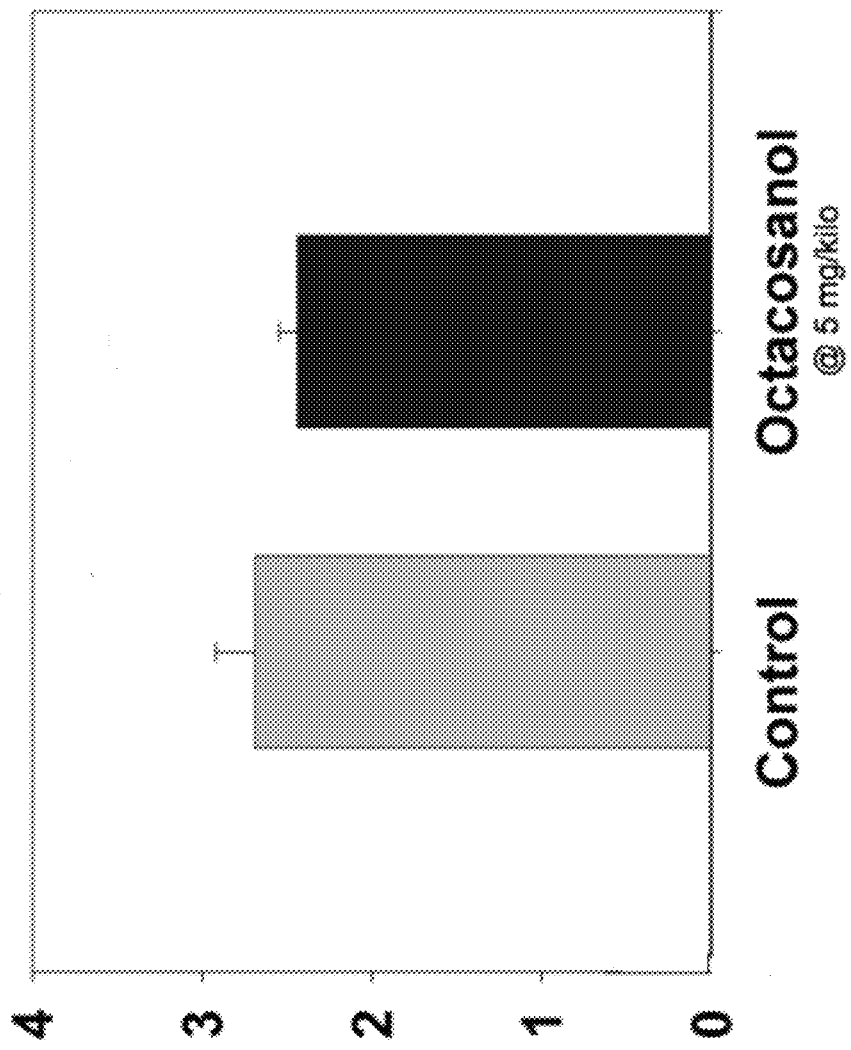
FIG. 22 shows levels of total cholesterol/HDL ratio in untreated rats and rats treated with particles of the invention 5 mg/kg.
Figure 23:
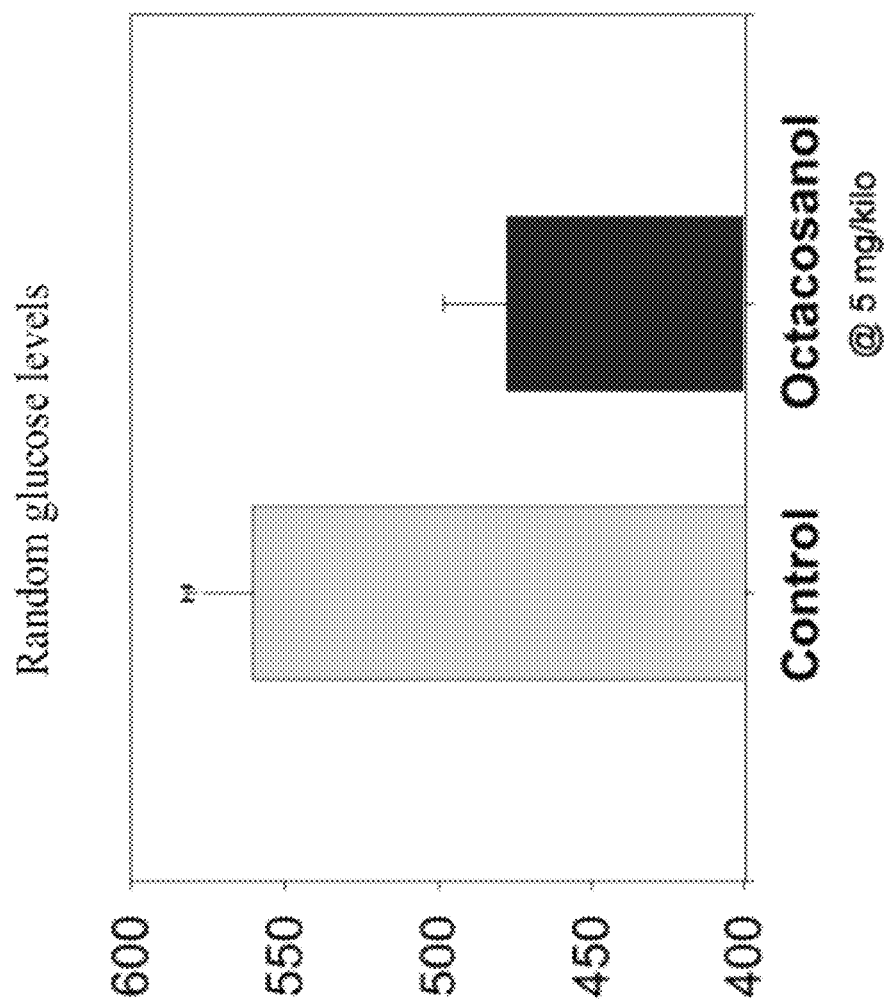
FIG. 23 shows random glucose levels in untreated rats and rats treated with particles of the invention at 5 mg/kg.
Figure 24:
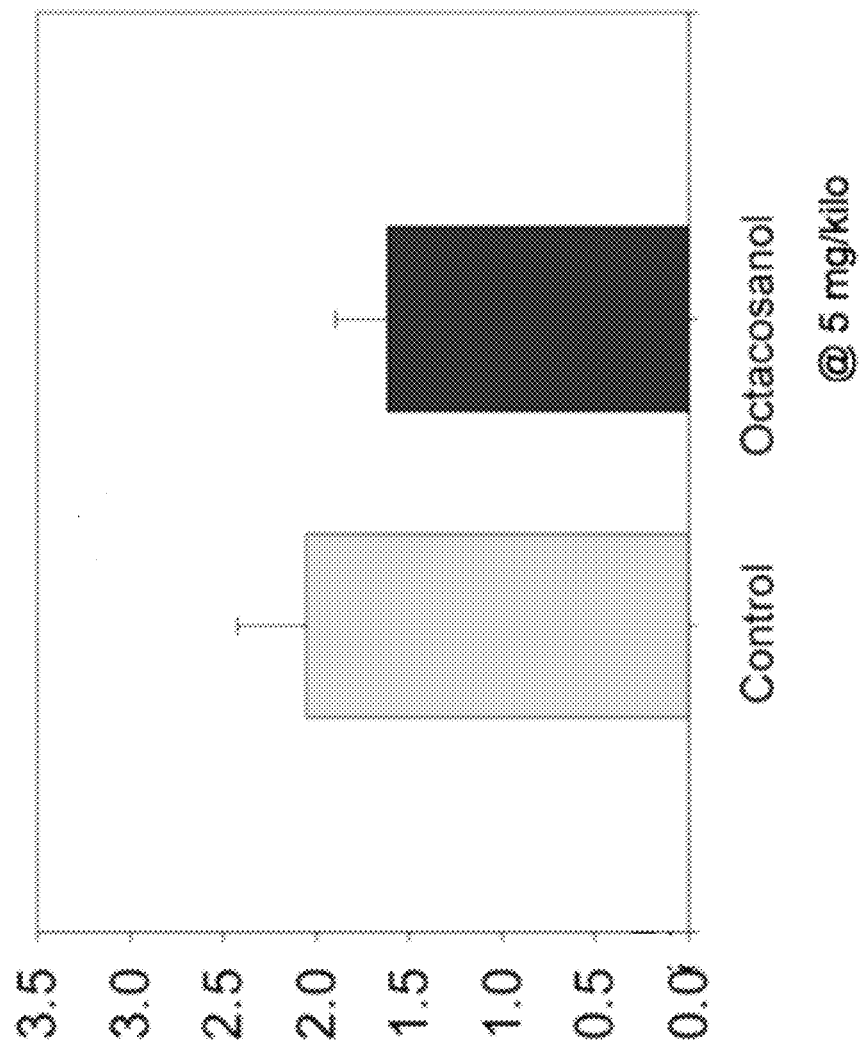
FIG. 24 shows fasting insulin levels in untreated rats and rats treated with particles of the invention at 5 mg/kg.
Figure 25:
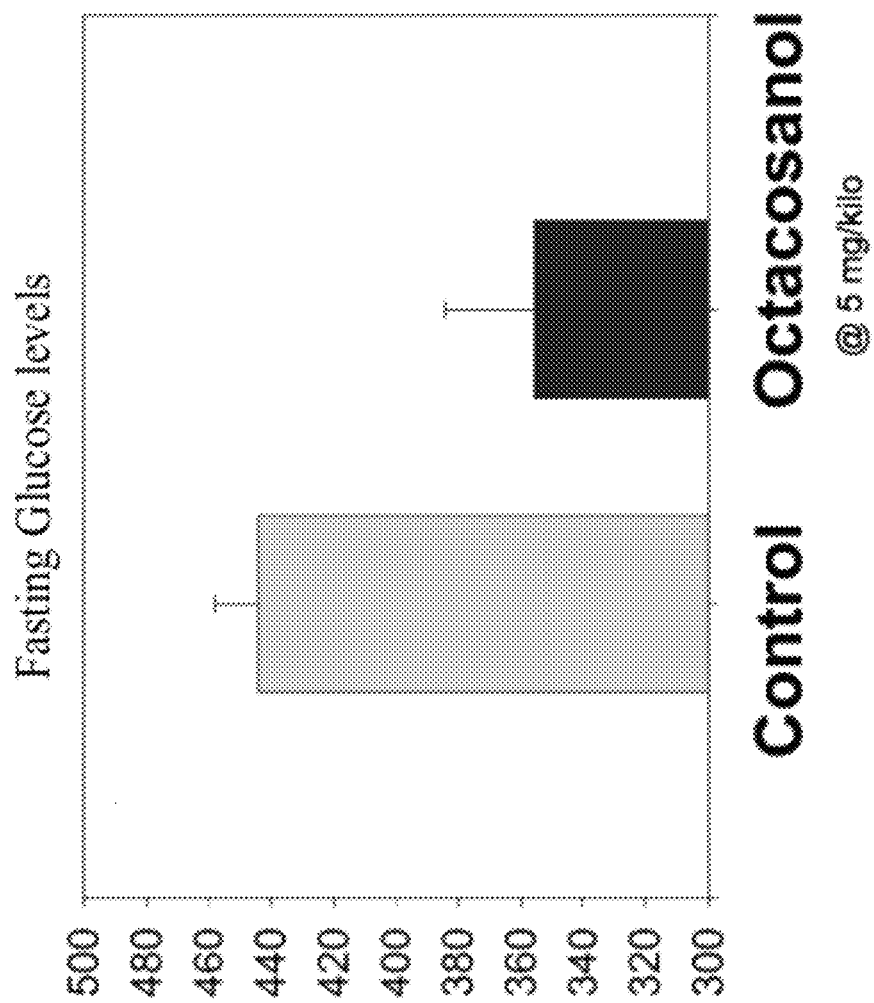
FIG. 25 shows fasting glucose levels in untreated rats and rats treated with particles of the invention at 5 mg/kg.
Figure 26:
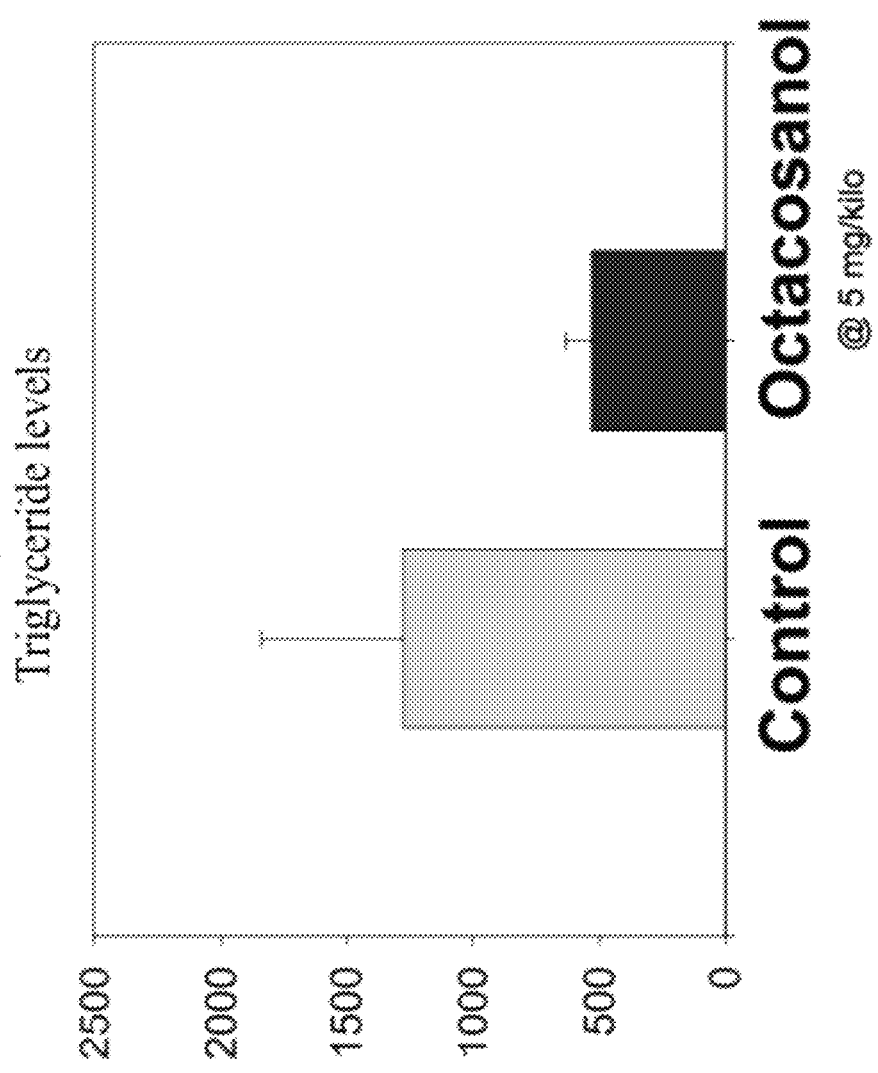
FIG. 26 shows triglyceride levels in untreated rats and rats treated with particles of the invention at 5 mg/kg.
Figure 27:
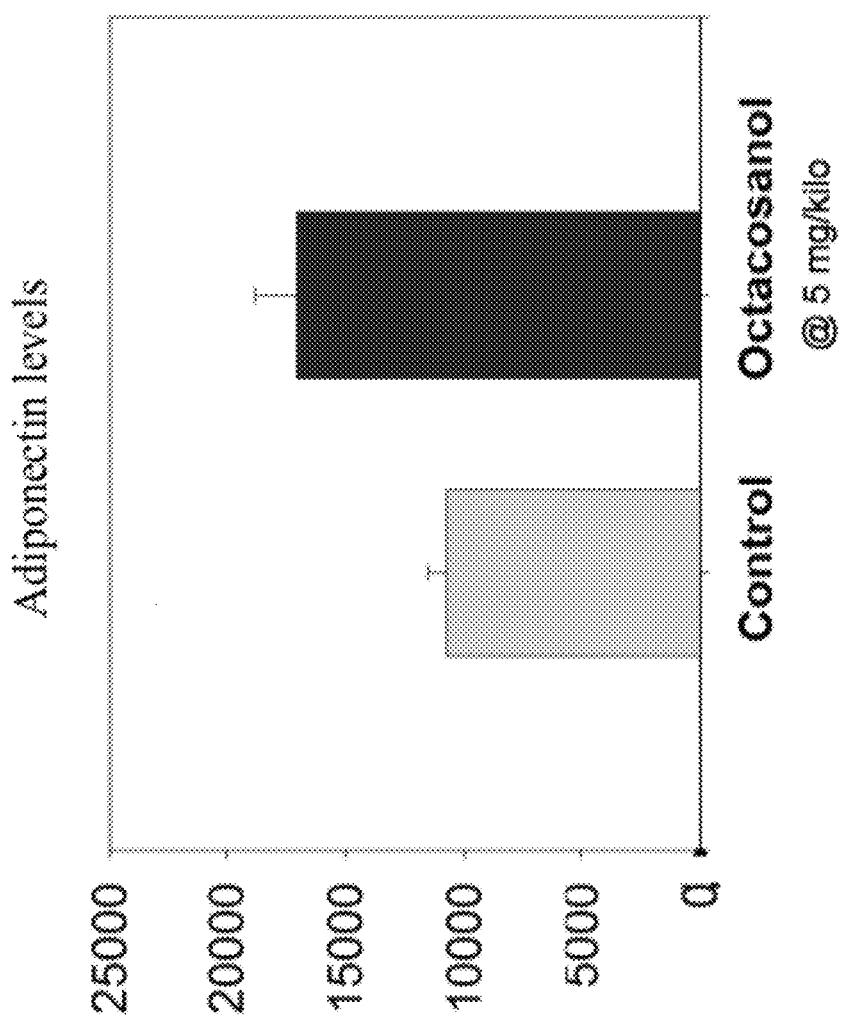
FIG. 27 shows adiponectin levels in untreated rats and rats treated with particles of the invention at 5 mg/kg.
Figure 28:
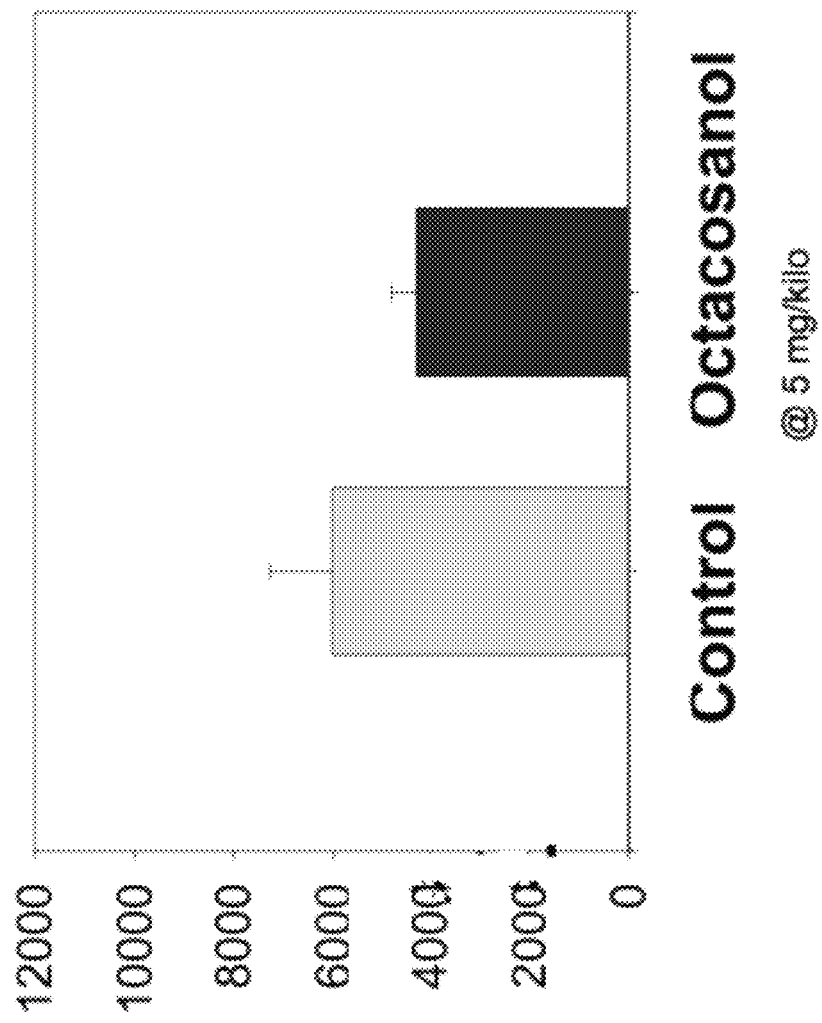
FIG. 28 shows MCP-1 (monocyte chemotactic protein-1) levels in untreated rats and rats treated with particles of the invention 5 mg/kg.
Figure 29:
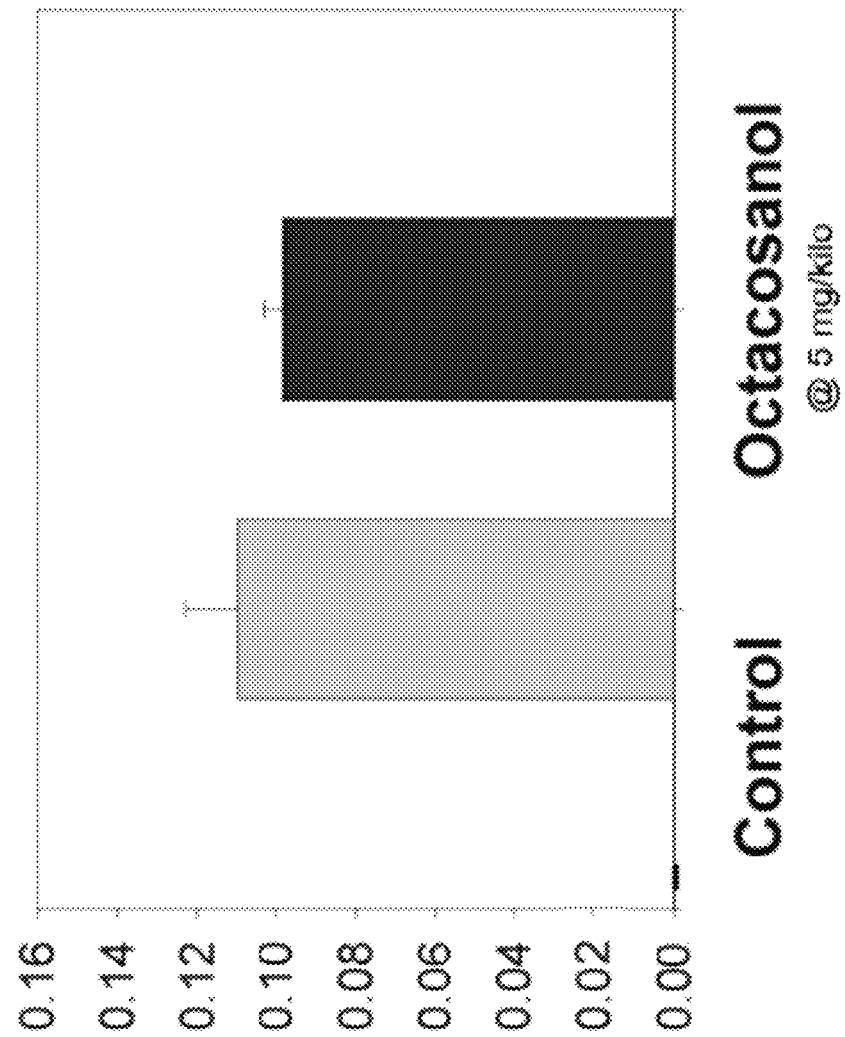
FIG. 29 shows protein oxidation levels in untreated rats and rats treated with particles of the invention at 5 mg/kg.

Unless defined otherwise, all technical and scientific terms used herein generally have the same meaning as commonly understood by one of ordinary skill in the art to which this invention belongs.

The term "policosanol" refers to a mixture of concentrated N-alkyl alcohols. Exemplary sources of policosanol are sugar cane and bees wax. The policosanols are extracted by known methods. The long chain alcohols in policosanol are primarily 1-Octacosanol, 1-Triacontanol, 1-Tetracosanol, and 1-Hexacosanol. Typical commercially available commercial compositions are composed of 90% minimum fatty alcohols of (a) 1-Tetracosanol: 0-10%; (b) 1-Hexacosanol: 2-15%; (c) 1-Heptacosanol: 0-0.5%; (d) 1-Octacosanol: 50-70%; (e) 1-Nonacosanol: 0-10%; (f) 1-Triacontanol: 5-20%; (g) 1-Dotriacontanol: 0.1-10%; and (h) 1-Tetratriacontanol: 0.1-10%.

The terms "effective average particle size," "particle size" and "size" are used interchangeably. The terms refer to the particle size essentially corresponding to the apex of a peak produced in an assessment of particle size using light scattering. Useful methods for determining the size of the particles of the invention are not limited to light scattering.

The methods and formulations may be used for prophylactic or therapeutic purposes. In some embodiments, the terms "treating" or "treatment" of any disease or disorder refers to ameliorating the disease or disorder (i.e., arresting or reducing the development of the disease or at least one of the clinical symptoms thereof). In other embodiments, "treating" or "treatment" refers to ameliorating at least one physical parameter, which may not be discernible by the subject. In yet other embodiments, "treating" or "treatment" refers to inhibiting the disease or disorder, either physically, (e.g., stabilization or eradication of a discernible symptom), physiologically, (e.g., stabilization or eradication of a physical parameter) or both. In still other embodiments, "treating" or "treatment" refers to delaying the onset of the disease or disorder.

"Therapeutically effective amount" is used interchangeably herein with "an amount effective to," when referring to a method of the invention. When used in reference to a policosanol dosage, these terms refer to a dosage that provides the specific pharmacological response for which the policosanol is administered in a significant number of subjects in need of such treatment. It is emphasized that "therapeutically effective amount," administered to a particular subject in a particular instance may not be effective for 100% of patients treated for a specific disease, and will not always be effective in treating the diseases described herein, even though such dosage is deemed a "therapeutically effective amount" by those skilled in the art. It is to be further understood that policosanol dosages are, in particular instances, measured as oral dosages, or with reference to drug levels as measured in blood.

As used herein, the terms "individual," "subject," and "patient," are used interchangeably to refer to an animal, e.g. a mammal, e.g. a human.

A. The Compositions

In various embodiments, the invention provides a nanoparticle of policosanol. A representative nanoparticle of the invention includes a policosanol fraction comprising about 50% to 69% octacosanol and a stabilizer fraction. In an exemplary embodiment, the stabilizer fraction includes a poly(ethylene glycol) ester. In various embodiments, the stabilizer fraction includes a tocopheryl ester. Exemplary components of the stabilizer fraction include tocopheryl poly(ethylene glycol) esters, e.g., tocopheryl polyethylene glycol (1000) succinate ("TPGS"). Exemplary nanoparticles of the invention have a diameter of less than about 100 nm. Also provided are formulations incorporating a plurality of the nanoparticles of the invention, including pharmaceutical formulations.

In various embodiments, the invention provides a nanoparticle of octacosanol. A representative nanoparticle of the invention includes a policosanol fraction comprising about 95% to 100% octacosanol and a stabilizer fraction. In an exemplary embodiment, the stabilizer fraction includes a poly(ethylene glycol) ester. In various embodiments, the stabilizer fraction includes a tocopheryl ester. Exemplary components of the stabilizer fraction include tocopheryl poly (ethylene glycol) esters, e.g., tocopheryl polyethylene glycol (1000) succinate ("TPGS"). Exemplary nanoparticles of the invention have a diameter of less than about 100 nm. Also provided are formulations incorporating a plurality of the nanoparticles of the invention, including pharmaceutical formulations.

In various embodiments, the nanoparticles include a policosanol fraction that includes at least about 50% octacosanol, at least about 51% octacosanol, at least about 52% octacosanol, at least about 53% octacosanol, at least about 54% octacosanol, at least about 55% octacosanol, at least about 56% octacosanol, at least about 57% octacosanol, at least about 58% octacosanol, at least about 59% octacosanol, at least about 60% octacosanol, at least about 61% octacosanol, at least about 62% octacosanol, at least about 63% octacosanol, at least about 64% octacosanol, at least about 65% octacosanol or at least about 66% octacosanol, at least about 67% octacosanol, at least about 68% octacosanol, at least about 69% octacosanol, In various embodiments, the nanoparticles include a policosanol fraction that includes not more than about 69% octacosanol, not more than about 68% octacosanol, not more than about 67% octacosanol, not more than about 66% octacosanol, not more than about 65% octacosanol, not more than about 64% octacosanol, not more than about 63% octacosanol, not more than about 62% octacosanol, not more than about 61% octacosanol, not more than about 60% octacosanol, not more than about 59% octacosanol, not more than about 58% octacosanol, not more than 57% octacosanol, not more than 56% octacosanol, not more than 55% octacosanol, not more than 54% octacosanol, not more than 53% octacosanol, not more than 52% octacosanol, not more than 51% octacosanol, or not more than 50% octacosanol.

In an exemplary embodiment, the nanoparticles include a policosanol fraction having octacosanol in the range from about 50% to about 69%, from about 51% to about 68%, from about 52% to about 67%, from about 53% to about 66%, from about 54% to about 65%, from about 55% to about 64%, from about 56% to about 63%, from about 57% to about 62%, from about 58% to about 61%, from about 59% to about 60%, or about 60%.

In various embodiments, the policosanol fraction includes both octacosanol and triacontanol. In an exemplary embodiment, the policosanol used has an octacosanol-triacontanol ratio from about 2:1 to about 7:1, from about 3:1 to about 6:1, from about 4:1 to about 5:1, from about 6:1 to about 7:1, In various embodiments, the policosanol fraction includes both octacosanol and hexacosanol. In an exemplary embodiment, the policosanol used has an octacosanol:hexacosanol ratio ranging from about 4:1 to about 9:1; from about 5:1 to about 8:1; from about 6:1 to about 7:1; from about 7:1 to about 8:1; from about 8:1 to about 9:1;

In various embodiments, the policosanol fraction includes both triacontanol and hexacosanol. In an exemplary embodiment, the policosanol used has a triacontanol:hexacosanol ratio of at most about 4:1; at most about 3:1; at most about 2:1; at most about 1:1; at most about 0.8:1; at most about 0.6:1; or at most about 4:1.

In an exemplary embodiment, the nanoparticles include a policosanol fraction that includes from 50% to about 69% octacosanol in admixture with triacontanol at a ratio of about 2:1 to about 7:1 and a stabilizer fraction that is essentially completely formed from TPGS (e.g., at least about 90%, 91%, 92%, 93%, 94%, 95%, 96%, 97% 98% or 99% TPGS). In various embodiments, the policosanol fraction and TPGS are in a ratio of about 1:2.8.

In various embodiments, the invention provides a nanoparticle of octacosanol. A representative nanoparticle of the invention includes a policosanol fraction comprising about 95% to 100% octacosanol and a stabilizer fraction. In an exemplary embodiment, the stabilizer fraction includes a poly(ethylene glycol) ester. In various embodiments, the stabilizer fraction includes a tocopheryl ester. Exemplary components of the stabilizer fraction include tocopheryl poly(ethylene glycol) esters, e.g., tocopheryl polyethylene glycol (1000) succinate ("TPGS"). Exemplary nanoparticles of the invention have a diameter of less than about 100 nm. Also provided are formulations incorporating a plurality of the nanoparticles of the invention, including pharmaceutical formulations.

In various embodiments, the nanoparticles include a policosanol fraction that includes at least about 95% octacosanol, at least about 96% octacosanol, at least about 97% octacosanol, at least about 98% octacosanol, at least about 99% octacosanol, at least about 100% octacosanol.

In various embodiments, the nanoparticles include a policosanol fraction that includes not more than about 100% octacosanol, not more than about 99% octacosanol, not more than about 98% octacosanol, not more than about 97% octacosanol, not more than about 96% octacosanol, not more than about 95% octacosanol.

In an exemplary embodiment, the nanoparticles include a policosanol fraction having octacosanol in the range from about 95% to about 100%, from about 95% to about 96%, from about 96% to about 97%, from about 98% to about 99%, or about 100%.

In various embodiments, the policosanol fraction includes both octacosanol and triacontanol. In an exemplary embodiment, the policosanol used has an octacosanol-triacontanol ratio from about 45:1 to about 99:1

In various embodiments, the policosanol fraction includes both octacosanol and hexacosanol. In an exemplary embodiment, the policosanol used has an octacosanol:hexacosanol ratio ranging from about 40:1 to about 99:0.5.

In various embodiments, the policosanol fraction includes both triacontanol and hexacosanol. In an exemplary embodiment, the policosanol used has a triacontanol:hexacosanol ratio of at most about 2:1, at most about 1:1; at most about 0.8:1; at most about 0.6:1; or at most about 2:1.

In an exemplary embodiment, the nanoparticles include a policosanol fraction that includes from 95% to about 100% octacosanol in admixture with triacontanol at a ratio of about 45:1 to about 99:0.5 and a stabilizer fraction that is essentially completely formed from TPGS (e.g., at least about 95%, 96%, 97%, 98%, 99%, 99% TPGS). In various embodiments, the octacosanol fraction and TPGS are in a ratio of about 1:2.8.

The present invention makes use of policosanol or a component of policosanol acquired or isolated from any appropriate source. For example, U.S. Pat. Nos. 5,663,156; 5,856,316; 6,197,832; 6,225,354; and 6,596,776, all of which are incorporated herein by reference, disclose policosanol compositions that are specific to the starting material and extraction processes used. In various embodiments, the policosanol of use in making a nanoparticle of the invention includes at least about 50% octacosanol, at least about 51% octacosanol, at least about 52% octacosanol, at least about 53% octacosanol, at least about 54% octacosanol, at least about 55% octacosanol, at least about 56% octacosanol, at least about 57% octacosanol, at least about 58% octacosanol, at least about 59% octacosanol or at least about 60% octacosanol. In various embodiments, the policosanol used includes between about 60% and about 69% octacosanol. In an exemplary embodiment, the amount of octacosanol is from about 57% to about 58%.

The present invention makes use of policosanol or a component of policosanol acquired or isolated from any appropriate source. For example, U.S. Pat. Nos. 5,663,156; 5,856,316; 6,197,832; 6,225,354; and 6,596,776, all of which are incorporated herein by reference, disclose policosanol compositions that are specific to the starting material and extraction processes used. In various embodiments, the policosanol of use in making a nanoparticle of the invention includes at least about 95% octacosanol, at least about 96% octacosanol, at least about 97% octacosanol, at least about 99% octacosanol, at least about 99% octacosanol, at least about 100% octacosanol. In various embodiments, the policosanol used includes between about 91% and about 100% octacosanol. In an exemplary embodiment, the amount of octacosanol is from about 98% to about 99%.

Various exemplary surfactants of use as a stabilizer fraction in the nanoparticle of the invention and its formulations include vitamin E TPGS (tocopherol propylene glycol succinate, a water-soluble form of vitamin E), sorbitan monolaurate (Span 20), sorbitan monopalmitate (Span 40), poloxamer, sorbitan monostearate (Span 60), sorbitan monooleate (Span 80), polyoxyethylene (20) sorbitan monolaurate (Tween 20, polysorbate 20), polyoxyethylene (20) monopalmitate (Tween 40, polysorbate 40), polyoxyethylene (20) monostearate (Tween 60, polysorbate 60), polyoxyethylene (20) tri-stearate (Tween 65, polysorbate 65), polyoxyethylene (20) monooleate (Tween 80, polysorbate 80), sucrose monomyristate, sucrose palmitate/stearate, sucrose stearate, dioctylsulfosuccinate sodium salt, monoglyceride monooleate, monoglyceride monolaurate, monoglyceride monopalmitate, lecithin, diglyceride mixtures, citric acid esters of monoglycerides, acetic acid esters of monoglycerides, lactic acid esters of monoglycerides, diacetyl tartaric esters of monoglycerides, polyglycerol esters of fatty acids, cyclodextrins, propylene glycol esters of fatty acids, stearoyl lactylates, $C_{8-18}$ free fatty acids, PTS (U.S. Pat. No. 6,045,826) or combinations thereof. In various embodiments, the stabilizer fraction does not include a cyclodextrin. In other embodiments, the stabilizer fraction does not include a polyoxyethylene sorbitan fatty acid ester.

The nanoparticles of the invention can include any useful ratio of policosanol fraction to stabilizer fraction that provides a nanoparticle having a diameter of less than or equal to about 100 nm. In an exemplary embodiment, the ratio of policosanol fraction:stabilizer fraction is from about 1:1 to about 1:4, for example, from about 1:2 to about 1:3.5. Similarly, in various embodiments, the ratio of octacosanol:stabilizer ranges from about 1:1.6 to about 1:3.5, for example, from about 1:2 to about 1:2.5. In an exemplary embodiment, the ratio is about 1:2.8. The ratio of triacontanol:stabilizer in exemplary nanoparticles of the invention ranges from about 1:5 to about 1:30, for example, from about 1:6: to about 1:30. In an exemplary embodiment, the stabilizer is an ester of vitamin E, such as TPGS (d-alpha-tocopheryl polyethylene glycol 1000 succinate).

Nanoparticles of the invention can include any useful ratio of policosanol fraction to stabilizer fraction that provides a nanoparticle having a diameter of less than or equal to about 100 nm. In an exemplary embodiment, the ratio of policosanol fraction:stabilizer fraction is from about 1:1 to about 1:4, for example, from about 1:2 to about 1:3.5. Similarly, in various embodiments, the ratio of Policosanol:stabilizer ranges from about 1:1.6 to about 1:3.5, for example, from about 1:2 to about 1:2.5. In an exemplary embodiment, the ratio is about 1:2.8. The ratio of triacontanol:stabilizer in exemplary nanoparticles of the invention ranges from about 1:225 to about 1:3000, for example, from about 1:200: to about 1:3000. In an exemplary embodiment, the stabilizer is an ester of vitamin E, such as TPGS (d-alpha-tocopheryl polyethylene glycol 1000 succinate).

The mixture from which the nanoparticles are produced can also include a surfactant in addition to the stabilizer fraction. Exemplary surfactants are set forth above and are generally known to those of skill in the art, e.g., TWEEN 20, TWEEN 80, esters (e.g., sucrose esters of palmitate and stearic acid monoesters), pectin, agar and the like.

The resultant nanoparticulate policosanol formulation can be utilized in solid or liquid dosage formulations, such as liquid dispersions, gels, aerosols, ointments, creams, controlled release formulations, fast melt formulations, lyophilized formulations, tablets, capsules, delayed release formulations, extended release formulations, pulsatile release formulations, mixed immediate release and controlled release formulations, etc.

Nanoparticles and pharmaceutical formulations according to the invention may also comprise one or more binding agents, filling agents, lubricating agents, suspending agents, sweeteners, flavoring agents, preservatives, buffers, wetting agents, disintegrants, effervescent agents, and other excipients. Such excipients are known in the art.

Exemplary excipient(s) that can be used in a nanoparticle or a formulation of the nanoparticles include, but are not limited to, soybean lecithin, soybean lecithin derivatives, caprylocaproyl macrogol-8 glycerides, medium chain triglycerides, refined olive oil, liquid flavors, polyoxyethylene sorbitan fatty acid esters, sugar esters, polyoxyethylene alkyl ethers, propylene glycol, dexpanthenol, almond oil, rice oil, sunflower oil, soybean oil, sesame oil, glycerin, glyceryl palmitostearate, sweet almond oil, oleic acid, polyglyceryl oleate, saccharose, poloxamer, macrogol-15 hydroxystearate, sorbitan fatty acid ester, ascorbyl palmitate, polethylene glycol, ceralution F, ceralution H, ceralution C, lauroyl macrogol-32 glycerides, glycerides, $C_{12}$-$C_{18}$ mono-, di- and triglycerides, glyceryl stearate, propylene glycol laureate, propylene glycol caprylate, propylene glycol dipergonate. In some embodiments, the formulation includes one or more excipients selected from citric acid anhydrous, potassium sorbate, sodium benzoate, and sucrose laureate.

Examples of filling agents are lactose monohydrate, lactose anhydrous, and various starches; examples of binding agents are various celluloses and cross-linked polyvinylpyrrolidone, microcrystalline cellulose, such as Avicel™, PH101 and Avicel™ PH102, microcrystalline cellulose, and silicified microcrystalline cellulose (ProSolv SMCC™).

Suitable lubricants, including agents that act on the flowability of the powder to be compressed, are colloidal silicon dioxide, such as Aerosil™200, talc, stearic acid, magnesium stearate, calcium stearate, and silica gel.

Examples of sweeteners are any natural or artificial sweetener, such as sucrose, xylitol, sodium saccharin, cyclamate, aspartame, and acsulfame. Examples of flavoring agents are Magnasweet™ (trademark of MAFCO), bubble gum flavor, and fruit flavors, and the like.

Examples of preservatives are potassium sorbate, methylparaben, propylparaben, benzoic acid and its salts, other esters of para hydroxybenzoic acid such as butylparaben, alcohols such as ethyl or benzyl alcohol, phenolic compounds such as phenol, or quaternary compounds such as benzalkonium chloride. Exemplary preservatives include, but are not limited to, potassium nitrite, sodium nitrite, benzoic acid, sodium benzoate, potassium benzoate and calcium benzoate Suitable diluents include pharmaceutically acceptable inert fillers, such as microcrystalline cellulose, lactose, dibasic calcium phosphate, saccharides, and/or mixtures of any of the foregoing. Examples of diluents include microcrystalline cellulose, such as Avicel™ PH101 and Avicel™ PH102; lactose such as lactose monohydrate, lactose anhydrous, and Pharmatose™ DCL21; dibasic calcium phosphate such as Emcompress™; mannitol; starch; sorbitol; sucrose; and glucose.

Suitable disintegrants include lightly cross linked polyvinyl pyrrolidone, corn starch, potato starch, maize starch, and modified starches, croscarmellose sodium, cross-povidone, sodium starch glycolate, and mixtures thereof.

Examples of effervescent agents are effervescent couples such as an organic acid and a carbonate or bicarbonate. Suitable organic acids include, for example, citric, tartaric, malic, fumaric, adipic, succinic, and alginic acids and anhydrides and acid salts. Suitable carbonates and bicarbonates include, for example, sodium carbonate, sodium bicarbonate, potassium carbonate, potassium bicarbonate, magnesium carbonate, sodium glycine carbonate, L-lysine carbonate, and arginine carbonate. Alternatively, only the sodium bicarbonate component of the effervescent couple may be present.

In various embodiments, the compositions of the invention contain nanoparticulate policosanol nanoparticles, which have an average particle size of less than about 100 nm, less than about 90 nm, less than about 80 nm, less than about 70 nm, less than about 60 nm, or less than about 50 nm, as measured by light-scattering methods, microscopy, or other appropriate methods.

In one embodiment of the invention, there is provided a formulation in which at least 99% of the policosanol nanoparticles have a particle size less than about 100 nm, less than about 90 nm, less than about 80 nm, less than about 70 nm, less than about 60 nm, or less than about 50 nm, when measured by the above-mentioned methods.

In one embodiment of the invention, there is provided a formulation in which at least 95% of the policosanol nanoparticles have a particle size less than about 100 nm, less than about 90 nm, less than about 80 nm, less than about 70 nm, less than about 60 nm, or less than about 50 nm, when measured by the above-mentioned methods.

In one embodiment of the invention, there is provided a formulation in which at least about 90% of the policosanol nanoparticles have a particle size less than about 100 nm, less than about 90 nm, less than about 80 nm, less than about 70 nm, less than about 60 nm, or less than about 50 nm, when measured by the above-mentioned methods.

In one embodiment of the invention, there is provided a formulation in which at least about 85% (e.g., from about 85% to about 99%, 95%, or 90%) of the policosanol nanoparticles have a particle size less than about 100 nm, less than about 90 nm, less than about 80 nm, less than about 70 nm, less than about 60 nm, or less than about 50 nm, when measured by the above-mentioned methods.

In one embodiment of the invention, there is provided a formulation in which at least about 80% (e.g., from about 80% to about 99%, 95%, 90%, or 85%) of the policosanol nanoparticles have a particle size less than about 100 nm, less than about 90 nm, less than about 80 nm, less than about 70 nm, less than about 60 nm, or less than about 50 nm, when measured by the above-mentioned methods.

In one embodiment of the invention, there is provided a formulation in which at least about 75% (e.g., from about 75% to about 99%, 95%, 90%, 85%, or 80%) of the policosanol nanoparticles have a particle size less than about 100 nm, less than about 90 nm, less than about 80 nm, less than about 70 nm, less than about 60 nm, or less than about 50 nm, when measured by the above-mentioned methods.

In one embodiment of the invention, there is provided a formulation in which at least about 70% (e.g., from about 70% to about 99%, 95%, 90%, 85%, 80%, or 70%) of the policosanol nanoparticles have a particle size less than about 100 nm, less than about 90 nm, less than about 80 nm, less than about 70 nm, less than about 60 nm, or less than about 50 nm, when measured by the above-mentioned methods.

In one embodiment of the invention, there is provided a formulation in which at least about 65% (e.g., from about 65% to about 99%, 95%, 90%, 85%, 80%, 75%, or 70%) of the policosanol nanoparticles have a particle size less than about 100 nm, less than about 90 nm, less than about 80 nm, less than about 70 nm, less than about 60 nm, or less than about 50 nm, when measured by the above-mentioned methods.

In one embodiment of the invention, there is provided a formulation in which at least about 60% (e.g., from about 60% to about 99%, 95%, 90%, 85%, 80%, 75%, or 65%) of the policosanol nanoparticles have a particle size less than about 100 nm, less than about 90 nm, less than about 80 nm, less than about 70 nm, less than about 60 nm, or less than about 50 nm, when measured by the above-mentioned methods.

In one embodiment of the invention, there is provided a formulation in which at least 55% (e.g., from about 55% to about 99%, 95%, 90%, 85%, 80%, 75%, 70%, 65%, or 60%) of the policosanol nanoparticles have a particle size less than about 100 nm, less than about 90 nm, less than about 80 nm, less than about 70 nm, less than about 60 nm, or less than about 50 nm, when measured by the above-mentioned methods.

Methods to determine the size of the nanoparticle are well known in the art. For example, optical diffraction (i.e. optical scatterometry) techniques can be used. These techniques include broadband scatterometry (U.S. Pat. Nos. 5,607,800; 5,867,276 and 5,963,329), spectral ellipsometry (U.S. Pat. No. 5,739,909) as well as spectral and single-wavelength beam profile reflectance and beam profile ellipsometry (U.S. Pat. No. 6,429,943). In addition it may be possible to employ single-wavelength laser BPR or BPE to obtain CD measurements on isolated lines or isolated vias and mesas (See U.S. patent application Ser. No. 10/243,245, filed Sep. 13, 2002).

In an exemplary embodiment, the invention provides a unit dosage formulation of policosanol nanoparticles of the invention containing a therapeutically effective amount of policosanol. In an exemplary embodiment, the unit dosage formulation is a formulation of nanoparticles containing a policosanol fraction and a stabilizer fraction and the unit dosage formulation includes from about 10 mg to about 100 mg, for example from about 10 mg to about 50 mg. In various embodiments, the unit dosage is a daily dosage. One of ordinary skill will appreciate that therapeutically effective amounts of policosanol can be determined empirically and can be employed in pure form or, where such forms exist, in pharmaceutically acceptable salt, ester, or pro-drug form. Actual dosage levels of policosanol in the nanoparticulate compositions of the invention may be varied to obtain an amount of the policosanol that is effective to obtain a desired therapeutic response for a particular composition and method of administration. The selected dosage level therefore depends upon the desired therapeutic effect, the route of administration, the potency of the administered policosanol, the desired duration of treatment, and other factors.

Dosage unit compositions may contain such amounts of such submultiples thereof as may be used to make up the daily dose. It will be understood, however, that the specific dose level for any particular patient will depend upon a variety of factors: the type and degree of the cellular or physiological response to be achieved; activity of the specific agent or composition employed; the specific agents or composition employed; the age, body weight, general health, sex, and diet of the patient; the time of administration, route of administration, and rate of excretion of the agent; the duration of the treatment; drugs used in combination or coincidental with the specific agent; and like factors well known in the medical arts.

In an exemplary method for making a nanoparticle of the invention, a pre-selected quantity of a stabilizer and policosanol are melted together with stirring to ensure homogeneity. Water or an aqueous solution of an additive, preservative, excipient, etc. at an elevated temperature is added to the melt, and maintained at a desired temperature, generally from about 60° C. to about 90° C. while stirring. In an exemplary method, the mixture of water to solids includes more water than solids, e.g., is approximately 10:1 by weight. The mixture is stirred while cooling to room temperature. In various embodiments, the method produces a suspension of the particles A. The Methods In addition to nanoparticles of policosanol and octacosanol and formulations including these nanoparticles, the present invention provides methods of using these nanoparticles and formulations to treat and prevent disease and to regulate metabolism. In various embodiments, the nanoparticles of the invention are of use to regulate hypertension, cholesterol metabolism and treat hyperlipidemia, hypercholesterolemia, inflammation, etc. In various embodiments, the formulations are use to regulate or reduce protein oxidation. In an exemplary embodiment, the formulation are of use to manage glycemic levels by reducing, insulin resistance, diabetes, and other conditions related to blood sugar levels. In still further embodiments, the formulations are of use to regulate, e.g., increase, plasma vitamin C levels and to reduce systolic and diastolic blood pressure. In other embodiments, the formulations are of use to inhibit PAI-1 (Plasminogen activation inhibitor). In other embodiments the formulations are of use in increasing DDP-IV that could be useful in cancer treatment.

In addition to nanoparticles of octacosanol and formulations including these nanoparticles, the present invention provides methods of using these nanoparticles and formulations to treat and prevent disease and to regulate metabolism. In various embodiments, the nanoparticles of the invention are of use to regulate hypertension, cholesterol metabolism and treat hyperlipidemia, hypercholesterolemia, inflammation, etc. In various embodiments, the formulations are use to regulate or reduce protein oxidation. In an exemplary embodiment, the formulation are of use to manage glycemic levels by reducing, insulin resistance, diabetes, and other conditions related to blood sugar levels. In still further embodiments, the formulations are of use to regulate, e.g., increase, plasma adiponectin and regulate body weight, and regulate VEGF (vascular endothelial growth factor) levels.

In an exemplary embodiment, the formulations are administered in a therapeutically effective amount to a subject to treat a particular disease or disorder and wherein the subject is not otherwise in need of treatment with a policosanol. In various embodiments, the nanoparticles are administered to treat a single disease or regulate a single metabolic factor. Thus, in an exemplary embodiment, the invention provides a method to treat insulin resistance in a subject not in need of treatment for hyperlipidemia, hypercholesterolemia, hypertension, etc. In an exemplary embodiment, the invention provides a method of regulating blood sugar in a subject not in need of treatment for hyperlipidemia, hypercholesterolemia, etc. In various embodiments, the invention provides a method of treating diabetes (e.g., Type II diabetes) in a subject not in need of treatment for hyperlipidemia, hypercholesterolemia, etc. In various embodiments, the invention provides a method to decrease or prevent protein oxidation in a subject who is not in need of treatment for treatment for hypertension, hyperlipidemia, hypercholesterolemia, etc. In an exemplary embodiment, the invention provides a method of increasing serum vitamin C levels in a subject not in need of treatment for hyperlipidemia, hypercholesterolemia, etc Non-limiting examples of methods of the invention are set forth below:

Protein Oxidation

The invention provides a method of decreasing protein oxidation in a subject and, therefore, reducing the deleterious consequences of this oxidation. The method includes administering to a subject a therapeutically effective amount of a policosanol formulation of the invention to decrease protein oxidation in a subject.

Oxidative stress has been implicated in the pathogenesis of acute and chronic diseases and injury in a variety of pathophysiological conditions such as hepatotoxin exposures, intrahepatic cholestasis, alcoholic liver injury, liver ischemia/reperfusion injury and viral hepatitis (Stehbens, *Exp. Ma Pathol;* 2003; 75(3): 265; Jaeschke et al., *Toxicol. Lett;* 2003; 144(3): 279-88; McDonough, *Toxicology.* 2003; 189(1-2): 89; Jaeschke et al., *J. Clin. Invest;* 1988; 81(4): 1240). Overproduction of reactive oxygen species (ROS) and nitrogen species (RNS), along with significant decrease of antioxidant defense in these pathological conditions, impairs various cellular functions through the processes of lipid per oxidation, protein oxidation and nucleic base oxidation. Lipid peroxidation, for example, causes changes in the physical and chemical properties of cellular membranes, thus altering their fluidity and permeability, leading to impairment in membrane signal transduction and ion exchange, resulting in swelling, cytolysis and finally cell death. The oxidation of proteins and DNA also relates directly to cellular dysfunction and death (Fang Y Z et al. Nutrition. 2002; 18(10): 872-9).

Diseases related to protein oxidation include, but are not limited to, rheumatoid arthritis (IgG, α-1-proteinase inhibitor), ischemia reperfusion injury, emphysema (α-1-proteinase inhibitor, elastase), neurodegenerative diseases (e.g., Alzheimer, Parkinson's), muscular dystrophy, disorders associated with aging (glutamine synthetase, carbonic anhydrase III, aconitase), acute pancreatitis, cataractogenesis (α-crystallins), cancer, chronic ethanol ingestion, adult respiratory distress syndrome. The formulations of the invention can also be used to treat or ameliorate the effects of Kwashiorkor (Manory, *J. Pediatr;* 2000; 137: 421).

An exemplary therapeutically relevant dose is one that leads to a reduction in a standard clinical marker of protein oxidation, e.g., protein carboxylation. Protein carbonyl content (PCC) is the most widely used marker of oxidative modification of proteins. There are several methodologies for the quantitation of PCC; in various conventional methods, 2,4-dinitrophenyl hydrazine is allowed to react with the protein carbonyls to form the corresponding hydrazone, which can be analyzed optically by radioactive counting or immunohistochemically. See, e.g., Yan et al., *Arch. Biochem. Biophys.* 327: 330-334, 1996.

In various embodiments, the nanoparticles of the invention are administered orally. In an exemplary embodiment, the nanoparticles are administered at a dosage of from about 10 mg to about 100 mg per day, for example, from about 10 mg to about 50 mg per day.

Increase in Serum Vitamin C

The invention also provides a method of increasing serum vitamin C in a subject. The method includes administering to a subject a therapeutically effective amount of a policosanol formulation of the invention to increase or regulate serum vitamin C levels in a subject.

Because insulin resistance and diabetes are accompanied by decreased serum vitamin C levels as compared to the levels observed in healthy subjects, orally administered supplemental vitamin C has been suggested as a treatment for the consequences of insulin resistance and diabetes, including endothelial dysfunction. However, supplemental vitamin C was not found to be effective when used alone (Kaneto et al., *Diabetes;* 1999; 48(12): 2398), quite possibly because orally administered vitamin C supplements does not improve endothelial dysfunction or insulin resistance (Chen et al., *Am. J. Physiol. Heart Circ. Physiol.;* 2006; 290(1): H137).

The present invention provides a method of regulating endogenous vitamin C and, therefore, a method of treating insulin resistance, diabetes and the consequences of these syndromes.

An exemplary therapeutically relevant dose is one that leads to an increase in a standard clinical marker of serum Vitamin C concentration, e.g., a sandwich ELISA method using commercially available kits from Fisher Thermo Scientific Co, Rockford, Ill. See, e.g., Washko et al., *Anal. Biochem.* 1992; 204:1-14.

In various embodiments, the nanoparticles of the invention are administered orally. In an exemplary embodiment, the nanoparticles are administered at a dosage of from about 10 mg to about 100 mg per day, for example, from about 10 mg to about 50 mg per day.

The invention provides a method of increasing VEGF levels in a subject and, therefore, reducing the deleterious consequences in diseases such as coronary artery disease, stroke, and chronic wounds. The method includes administering to a subject a therapeutically effective amount of an octacosanol formulation of the invention to increase VEGF levels in a subject.

Vascular endothelial growth facto (VEGF) is a sub-family of growth factors, specifically the platelet-derived growth factor family of cystine-knot growth factors. They are important signaling proteins involved in both vasculogenesis (the "de novo" formation of the embryonic circulatory system) and angiogenesis (the growth of blood vessels from pre-existing vasculature). Vascular endothelial growth factor (VEGF) is a chemical signal produced by cells that stimulates the growth of new blood vessels. It is part of the system that restores the oxygen supply to tissues when blood circulation is inadequate. (Folkman J. Harrision's Texbook of Internal Medicine, 15th McGraw-Hill, New York, N.Y., 2000 pp. 132-152).

VEGF's normal function is to create new blood vessels during embryonic development, new blood vessels after injury, and new vessels (collateral circulation) to bypass blocked vessels. The normal, healthy body maintains a perfect balance of angiogenesis modulators. In general, angiogenesis is "turned off" by the production of more inhibitors than stimulators. (Li V. et. all., The Role of Therapeutic Angiogenesis in Tissue Repair and Regeneration Adv Skin Wound Care 2005; 18:491-500).

When VEGF is overexpressed, it can contribute to disease. Excessive angiogenesis occurs in diseases such as cancer, diabetic blindness, age-related macular degeneration, rheumatoid arthritis, psoriasis, and more than 70 other conditions produce abnormal amounts of angiogenic growth factors, overwhelming the effects of natural angiogenesis inhibitors. Antiangiogenic therapies, aimed at halting new blood vessel growth, are used to treat these conditions.

Insufficient angiogenesis occurs in diseases such as coronary artery disease, stroke, and chronic wounds. In these conditions, blood vessel growth is inadequate, and circulation is not properly restored, leading to the risk of tissue death. Insufficient angiogenesis occurs when tissues cannot produce adequate amounts of angiogenic growth factors. Therapeutic angiogenesis, aimed at stimulating new blood vessel growth with growth factors, is being developed to treat these conditions. Angiogenic gene therapy is also being developed as a method to deliver angiogenic growth factors to the heart, limbs, and wounds. There are at least 30 known natural angiogenesis inhibitors found in the body Folkman, et. al (Journal of Experimental Medicine 1975; 141) demonstrated the first angiogenesis inhibitor molecule in a study of cartilage.

Angiogenesis-dependent disease was treated by using interferon alfa2a, an angiogenesis inhibitor, was used to regress the abnormal blood vessels growing in the lungs of a boy with a benign disease called pulmonary hemangiomatosis. (White et. al., (N Engl J Med 1992; 326:1456-1463)

Pro-angiogenic Therapy for the Ischemic heart disease has been demonstrated (Stegmann T. et. al., (Circulation 199897 (7):645-650)

VEGF can stimulate endothelial cells to synthesize osteogenic factors and thus indirectly promote bone formation (Sato K. et. al. Anabolic Endocrinology 1997; 138:2953-2962: Longaker M T. et. al., Plast Reconstr Surg 2002; 109: 2384-2397), Low levels of (VEGF) i has been implicated in diabetes (Gurtner, et. al., PNAS, 2009, vol. 106, 13505-13510). Both fibroblasts isolated from type 2 diabetic patients, and normal fibroblasts exposed chronically to high glucose, were defective in their capacity to up-regulate VEGF in response to hypoxia.

Exemplary markers of a "therapeutically effective amount" as used herein refers to the amount of octacosanol in a formulation of the invention which, upon administration (e.g., oral administration) raises VEGF levels in the subject, Insulin Resistance The present invention also provides a method of treating insulin resistance and the consequences arising out of insulin resistance including, but not limited to, diabetes. The method includes administering to a subject an amount of a particulate formulation of the invention sufficient to treat insulin resistance.

Insulin resistance is defined as an inadequate response by insulin target tissues, such as skeletal muscle, liver, and adipose tissue, to the physiologic effects of circulating insulin. The hallmarks of impaired insulin sensitivity in these three tissues are decreased insulin-stimulated glucose uptake into skeletal muscle, impaired insulin-mediated inhibition of hepatic glucose production in liver, and a reduced ability of insulin to inhibit lipolysis in adipose tissue. In fact, insulin resistance is a major predictor for the development of Type II diabetes.

In Type II diabetes, it has been widely established that insulin resistance precedes the development of overt hyperglycemia. The causes of insulin resistance can be genetic and/or acquired. Type II diabetes also predisposes patients to elevated cholesterol and cardiovascular disease. In Western cultures, the most common acquired factors causing insulin resistance are obesity, sedentary lifestyle, and aging, all of which are interrelated. In the presence of a robust compensatory insulin secretory response to insulin resistance, glucose levels can remain relatively normal. However, when insulin-producing pancreatic β cells can no longer compensate for the decreased tissue insulin sensitivity, glucose homeostasis deteriorates and impaired glucose tolerance and eventually Type II diabetes develop.

Common diseases or disorders associated with insulin resistance include acanthosis nigricans, acne vulgaris, allergies, asthma, Alzheimer's Disease, atherosclerosis, bipolar disorder, breast cancer, cardiovascular disease, cataracts, cervical cancer, depression, diabetes mellitus, dyslipidemia, fatty liver disease, childhood Type-2 diabetes, chronic fatigue, colon and rectal cancer, dandruff, Graves' disease, heart disease, high LDL cholesterol, high triglycerides, hirsutism, hypoglycemia, hypothyroidism, inflammation, kidney disease, low HDL cholesterol, lupus, neuropathy, neuritis, osteoporosis, pancreatic cancer, Parkinson's disease, polycystic ovary syndrome, prostate cancer, rheumatoid arthritis, scleroderma, seborrhea, strokes, and varicose veins.

In addition to the diseases and disorders set forth above, some of the main consequences of insulin resistance include, but are not limited to, Type 2 diabetes mellitus, hypertension, arteriosclerosis, polycystic ovarian syndrome, non-alcoholic fatty liver disease, disturbances in the function of the vascular endothelium, elevation of triglycerides and cholesterol, disturbances of clotting, disturbances in kidney function, disturbances in heart rhythm, and elevated uric acid levels.

An exemplary therapeutically relevant dose is one that leads to a decrease in a standard clinical marker of serum insulin resistance, e.g., insulin and insulin levels in the plasma can be determined by the sandwich ELISA method using commercially available kits from Fisher Thermo Scientific Co, Rockford, Ill.).

In various embodiments, the nanoparticles of the invention are administered orally. In an exemplary embodiment, the nanoparticles are administered at a dosage of from about 10 mg to about 100 mg per day, for example, from about 10 mg to about 50 mg per day.

Cholesterol-Related Diseases

In various embodiments, the present invention provides a method of treating hypercholesterolemia and/or regulating lipid metabolism in a subject. The method includes administering to a subject an amount of a nanoparticulate formulation of the invention sufficient to treat hypercholesterolemia.

Hypercholesterolemia, hyperlipidemia and cardiovascular disease are increasingly prevalent in Western industrial societies. The reasons for this are not completely understood, but may relate partly to a genetic predisposition to these conditions and partly to a diet high in saturated fats, together with an increasingly sedentary lifestyle as manual labor becomes increasingly less necessary. Hypercholesterolemia and hyperlipidemia are very significant, because they predispose individuals to cardiovascular disease, including atherosclerosis, myocardial infarction (heart attack), and stroke.

Specific forms of hyperlipidemia include, for example, hypercholesterolemia, familial dysbetalipoproteinemia, diabetic dyslipidemia, nephrotic dyslipidemia and familial combined hyperlipidemia. Hypercholesterolemia is characterized by an elevation in serum low-density lipoprotein-cholesterol and serum total cholesterol. Low-density lipoprotein (LDL cholesterol) transports cholesterol in the blood. Familial dysbetalipoproteinemia, also known as Type III hyperlipidemia, is characterized by an accumulation of very low-density lipoprotein-cholesterol (VLDL-cholesterol) particles called beta VLDLs in the serum. Also associated with this condition is a replacement of normal apolipoprotein E3 with abnormal isoform Apo lipoprotein E2. Diabetic dyslipidemia is characterized by multiple lipoprotein abnormalities, such as an overproduction of VLDL-cholesterol, abnormal VLDL triglyceride lipolysis, reduced LDL-cholesterol receptor activity and, on occasion, Type III hyperlipidemia. Nephrotic dyslipidemia, associated with malfunction of the kidneys, is difficult to treat and frequently includes hypercholesterolemia and hypertriglyceridemia. Familial combined hyperlipidemia is characterized by multiple phenotypes of hyperlipidemia, i.e., Type IIa, IIb, IV, V or hyperapobetalipoproteinemia.

It is well known that the likelihood of cardiovascular disease can be decreased if the serum lipids, and in particular HDL-cholesterol, can be increased. It is also well known that the progression of atherosclerosis can be retarded or the regression of atherosclerosis can be induced if total cholesterol to HDL ratio can be lowered. In such cases, individuals diagnosed with hyperlipidemia or hypercholesterolemia should consider lipid-lowering therapy to retard the progression or induce the regression of atherosclerosis for purposes of reducing their risk of cardiovascular disease, and in particular coronary artery disease. Such therapy will reduce the risk of stroke and myocardial infarction, among other consequences. In addition, certain individuals with what are considered normal serum lipid levels can develop cardiovascular disease. In these individuals other factors like lipid per oxidation and high levels of Lp(a) or lipoprotein A can lead to atherogenesis despite relatively normal cholesterol and lipid levels.

Exemplary markers of a "therapeutically effective amount" as used herein refers to the amount of policosanol in a formulation of the invention which, upon administration (e.g., oral administration) to the subject, maintains healthy serum lipid profiles, illustratively by raising HDL cholesterol, lowering the total cholesterol/HDL ratio, and/or lowering triglycerides, or aids in maintaining a healthy body weight.

Another exemplary therapeutically relevant dose is one that leads to a decrease of C-reactive protein, a standard clinical marker of lipid metabolism and cardiovascular risk factor.

Plasminogen Activation Inhibitor

In various embodiments, the present invention provides a method of regulating, e.g. lowering, the PAI-1 protein level in a subject. The method includes administering to a subject an amount of a nanoparticulate formulation of the invention sufficient to reduce the PAI-1 level in the subject. PAI-1 is a serine protease inhibitor that inhibits fibrinolysis by inactivating urokinase-type and tissue-type plasminogen activator. Plasma PAI-1 activity is highest between 12 midnight and 6 am. (Kluft C, et al., Thromb Haemost. 1988 Apr. 8; 59(2): 329-32).

PAI-1 is present in increased levels in various disease states (such as a number of forms of cancer), as well as in obesity and the metabolic syndrome. It has been linked to the increased occurrence of thrombosis in patients with these conditions. (Mimuro J (1991)"[Type 1 plasminogen activator inhibitor: its role in biological reactions]". Rinsho Ketsueki 32 (5): 487-9. PMID 1870265.): Binder B R, et al. (2002). "Plasminogen activator inhibitor 1: physiological and pathophysiological roles". News Physiol. Sci. 17: 56-61. PMID 11909993: Hoekstra T, et al., (2004). "Plasminogen activator inhibitor-type 1: its plasma determinants and relation with cardiovascular risk". Thromb. Haemost. 91 (5): 861-72: Lijnen H R (2005). "Pleiotropic functions of plasminogen activator inhibitor-1". J. Thromb. Haemost. 3 (1): 35 15; De Taeye B, et al., (2005). "Plasminogen activator inhibitor-1: a common denominator in obesity, diabetes and cardiovascular disease". Current opinion in pharmacology 5 (2): 149-54: Dellas C, Loskutoff D J (2005). "Historical analysis of PAI-1 from its discovery to its potential role in cell motility and disease". Thromb. Haemost. 93 (4): 631-40.

Retinol Binding Protein

In various embodiments, the present invention provides a method of regulating, e.g. lowering, the RBP-4 levels in a subject. The method includes administering to a subject an amount of a nanoparticulate formulation of the invention sufficient to reduce the RBP-4 levels in a subject and thereby treat diseases associated with elevated RBP-4 levels. Retinol binding protein 4 (RBP4) has recently been described as an adipokine that contributes to insulin resistance in the AG4KO mouse model. See Yang Q, et al., Serum retinol binding protein 4 contributes to insulin resistance in obesity and type 2 diabetes", Nature 436 (7049): 356-62. (2005). RBP4 is elevated in the serum before the development of diabetes and appears to identify insulin resistance and associated cardiovascular risk factors in subjects with varied clinical presentations. These findings provide a rationale for antidiabetic therapies aimed at lowering serum RBP4 levels. See Graham T E, et. al N Engl J. Med. 2006 Jun. 15; 354(24):2552-63.

Nitric Oxide

In various embodiments, the present invention provides a method of increasing nitric oxide levels in a subject. The method includes administering to a subject an amount of a nanoparticulate formulation of the invention sufficient to increase nitric oxide levels in a subject.

Endothelial NOS (eNOS), also known as nitric oxide synthase 3 (NOS3), generates NO in blood vessels and is involved with regulating vascular function and in reducing blood pressure. See Alderton W K, et al., Biochem J. 2001 Aug. 1; 357(Pt 3):593-615. NO is known to have various vascular effects, including direct vasodilatation (flow dependent and receptor mediated); indirect vasodilatation by inhibiting vasoconstrictor influences (e.g., inhibits angiotensin II and sympathetic vasoconstriction), anti-thrombotic effect (inhibits platelet adhesion to the vascular endothelium), anti-inflammatory effect (inhibits leukocyte adhesion to vascular endothelium), the ability to scavenge for superoxide anion; and anti-proliferative effect (e.g., inhibits smooth muscle hyperplasia).

Because of the above-mentioned actions of NO, its impaired production or reduced bioavailability can result in vasoconstriction (e.g., coronary vasospasm, elevated systemic vascular resistance, hypertension); thrombosis due to platelet aggregation and adhesion to vascular endothelium; inflammation due to up-regulation of leukocyte and endothelial adhesion molecules; vascular hypertrophy and stenosis. See Nitric Oxide: Biology and Pathobiology; By: Louis J. Ignarro (Editor) ISBN-10: 0123738660; ISBN-13: Publisher: Academic Press-2009. Diseases or conditions associated with abnormal NO production and bioavailability include, without limitation, hypertension; obesity; dyslipidemias (particularly hypercholesterolemia and hypertriglyceridemia); diabetes (types I and II); heart failure; atherosclerosis; and conditions associated with aging. See Dessy, C, et al., (September 2004). "Pathophysiological Roles of Nitric Oxide: In the Heart and the Coronary Vasculature" and Current Medical Chemistry—Anti-Inflammatory & Anti-Allergy Agents in Medicinal Chemistry (Bentham Science Publishers Ltd.) 3 (3): 207-216.

MCP-1 (Monocyte Chemotactic Protein-1)

In various embodiments, the present invention provides a method of regulating, e.g. lowering, the MCP-1 levels in a subject. The method includes administering to a subject an amount of a nanoparticulate formulation of the invention sufficient to reduce the MCP-1 levels in a subject and thereby treat diseases associated with elevated MCP-1 levels. MCP-1 is a chemokine that recruits monocytes to sites of inflammation. MCP-1 is expressed and secreted by adipocytes and stromal vascular cells in white adipose tissue. Obese rodents have higher circulating MCP-1 levels with increased adipose tissue expression of MCP-1. See J Biol. Chem. 2003 Nov. 21, 278(47): 46654-60. Furthermore, MCP-1 can directly contribute to insulin resistance by decreasing insulin stimulated glucose uptake and insulin induced insulin receptor tyrosine phosphorylation and can decrease the expression of adipogenic genes so as to inhibit adipocyte growth and differentiation.

Administration of MCP-1 to mice peripherally increases circulating monocytes, and increases monocyte accumulation in arteries with neo-intimal formation suggesting a role for MCP-1 in atherogenesis. See Cardiovasc Res. 2003 January; 57(1): 178-85.

ICAM-1 (Inter Cellular Adhesion Molecule-1)

In various embodiments, the present invention provides a method of regulating, e.g. reducing, elevated ICAM-1 levels in a subject. The method includes administering to a subject an amount of a nanoparticulate formulation of the invention sufficient to reduce ICAM-1 levels in a subject and thereby treat diseases associated with elevated ICAM-1 levels. ICAM-1 is the same receptor molecule used by the vast majority of viruses that cause the common cold. Rhinoviruses are the frequent cause of the common cold. Adhesion molecules play a major role in many fields of medicine including embryology, immunology, and malignancy.

Many physiological processes require that cells come into close contact with and adhere to other cells or the extracellular matrix. Cell-cell and cell-matrix interactions are mediated through several families of intercellular adhesion molecules or "ICAMs." See New Cell adhesion research, Patrick Nott and other contributors, ISBN-10: 1606923781; ISBN-13: 9781606923788 Publisher: Nova Biomedical Books-2009-04. ICAM-1 therefore plays an essential role in both normal and pathophysiological processes (Springer et al., 1987, Ann. Rev. Immunol. 5: 223-252). Strategies have therefore been developed to mediate cell adhesion by blocking ICAM-1 function or expression. Such strategies typically employ anti-ICAM-1 antibodies, ligands which competitively block ICAM-1 binding, or antisense nucleic acid molecules directed against ICAM-1 mRNA. However, the agents used in such therapies produce only a stoichiometric reduction in ICAM-1, and are typically overwhelmed by the abnormally high production of ICAM-1 by the diseased or activated cells.

Diseases characterized by infiltration of neutrophils are often associated with chronic conditions wherein ICAM-1 or VCAM-1 expression predominates. See Adams D H, Shaw S 1994 Leukocyte endothelial interactions and regulation of leukocyte migration. Lancet 343:831-836. An increase in local expression as well as in serum-soluble adhesion molecules has been reported in diverse pathologic conditions including arteriosclerosis, vasculitis, arthritis, renal and hepatic diseases, ischemia reperfusion conditions, organ rejection, metastasis, and many more pathologic conditions. See Bevilacqua M P, et al., 1994 Endothelial leukocyte adhesion molecules in human disease. Annu Rev Med 45:361-378.

Adhesion molecules may be important in specific forms of inflammation. See Gorski A 1994 the role of cell adhesion molecules in immunopathology. Immunol Today 15:251-255. What is needed, therefore, are agents in catalytic or sub-stoichiometric amounts which selectively inhibit expression of ICAM-1, in order to effectively decrease or block ICAM-1-mediated cell adhesion.

One of the many different ways of inhibiting viral infection is to stop the virus from binding to cells. Most of the rhinovirus serotypes use a single cellular receptor, i.e. the Intercellular Adhesion Molecule-1 (ICAM-1) for attachment to the cells. This could lead to the development of blockers of this receptor in an effort to find a cure for the common cold.

Expression of ICAM-1 has also been associated with a variety of inflammatory skin disorders such as allergic contact dermatitis, fixed drug eruption, lichen planus, and psoriasis. See Ho et al., 1990, J. Am. Acad. Dermatol. 22: 64-68; Griffiths and Nickoloff, 1989, Am. J. Pathology 135: 1045-1053; Lisby et al., 1989, Br. J. Dermatol. 120: 479-484; and Shiohara et al., 1989, Arch. Dermatol. 125: 1371-1376. In addition, ICAM-1 expression has been detected in patients with rheumatoid arthritis (Hale et al., 1989, Arth. Rheum. 32: 22-30); in pancreatic B-cells of diabetics (Campbell et al., 1989, P.N.A.S. USA 86: 4282-4286); in thyroid follicular cells of patients with Graves' disease (Weetman et al., 1989, J. Endocrinol. 122: 185-191); in renal and liver allograft rejection (Faull and Russ, 1989, Transplantation 48: 226-230; Adams et al., 1989, Lancet 1122-1125); and in inflammatory bowel disease (IBD) tissue (Springer T, 1990, Nature 346: 425-34).

Complications commonly observed in type I diabetes also involve expression of ICAM-1. For example, ICAM-1-mediated adhesion of leukocytes to capillary endothelium can cause microvascular ischemia in certain tissues of diabetics, such as the retina, peripheral nerves, and kidney. This results in capillary non-perfusion of these tissues, which in turn leads to diabetic retinopathy, neuropathy or nephropathy, or angiogenesis induced by adhesion between polymorphonuclear leukocyte and endothelial cell via intercellular adhesion molecule-1, (ICAM-1). It is therefore believed that inhibition of ICAM-1-mediated leukostasis can prevent retinal abnormalities associated with diabetes. See Miyamoto K et al. (2000), Am. J. Pathol. 156: 1733-1739; Miyamoto K et al. (1999), P.N.A.S USA 96:10836-1084; Jude E B et al. (1998), Diabetologia 41:330-6; Miyamoto et al. 1999, P.N.A.S USA 96: 10836-10841; and Yong Song Gho et. al Cancer Research 59, 5128-5132, Oct. 15, 1999.

DPPIV (DPP4, CD26) is a member of the class of proteases known as prolyl peptidases, which cleave proteins after proline residues (J. S. Rosenblum et al., Curr. Opin. Chem. Biol. 2003 7, 496). DPPIV, a serine dipeptidyl peptidase, cleaves the N-terminal X-Ala or X-Pro from target polypeptides, such as chemokines (e.g. CXCL11) and peptide hormones (e.g., glucagon-like peptide-1, GLP-1).

Dipeptidyl peptidase IV (DPP-IV) is involved in diverse biological processes such as cellular differentiation, T cell activation, and cell-matrix interaction. DPPIV inactivates certain growth factors, chemokines, and neuropeptides by peptide cleavage. It is widely expressed in various normal tissues including normal melanocytes, lung, and prostate epithelial cells. Thus it is emerging as a target for cancer and autoimmune diseases.

DPPIV possesses a transmembrane region and a very short cytoplasmic domain, but is often cleaved and released as a soluble, circulating form. It is found as a dimer with itself or with FAP (fibroblast activation protein-α, seprase), another prolyl peptidase. It also has non-peptidase functions: through its interaction with adenosine deaminase (ADA) and extracellular matrix components, it influences T-cell activation and proliferation (I. Ben-Shooshan et al. Biochem. Biophys. Acta 2002 1587 21). Though its role in diabetes is well known and drugs like januviaa in the market for diabetes (U.S. Pat. No. 7,026,316 B2, 2006). Interestingly DPPIV expression is markedly decreased or completely extinguished in cells derived from melanomas, lung cancer, prostate cancer, and tumorigenic, in vitro transformed epithelial cells. It has became a target of interest in cancer and auto immune diseases (Wesley U V. et. al., 2008. Frontiers in Bioscience 13, 2435-2443: B. Pro, et al., Histol Histopathol (2004) 19: 1345-1351; Havre P A, et. al., Front. Biosci. 13: 1634 15.). The results support the view that down regulation of DPPIV is an important event in progression of melanoma, lung, and prostate cancers. Re-expression of DPPIV using tetracycline inducible system, in melanomas and in non-small cell lung cancer cells, resulted in profound phenotypic changes that are characteristics of normal cells. DPPIV re-expression led to removal of block in differentiation, acquired dependence on exogenous growth factor for cell survival, and loss of tumorigenicity.

In vitro studies confirm that DPP-4 inhibition increases the metastatic potential of colon [Masur K, et al., Reg Pep. 2006; 137: 147-155. 5]. In addition, dipeptidyl peptidase inhibits the maligant phenotype of prostate cancer cells by blocking basic fibroblast growth factor signaling pathway. [Wesley U V, et al., Cancer Res. 2005; 65:1325-1334. 6]. A significant decrease in serum DPPIV activity has been reported in patients with oral cancers as compared to healthy subjects. (Uetmasu et al., J. Oral Pathol. Med. 27, 106-110). Patients with colorectal cancer (Cordero et al., 2000; Br. J. Cancer 83, 1139-1146.). have lower levels of serum CD26 than normal donors.

These results suggest that DPPIV is a tumor suppressor gene and, given the multiple functions of CD26 and its potential involvement in tumor biology, the development of therapeutic modalities targeting it may prove to be a useful strategy in the treatment of selected tumors.

In various embodiments, the nanoparticles of the invention are administered orally. In an exemplary embodiment, the nanoparticles are administered at a dosage of from about 10 mg to about 100 mg per day, for example, from about 10 mg to about 50 mg per day.

In various embodiments of each of the methods of the invention, including the exemplary methods set forth above, the subject treated with the formulations of the invention is not in need of vitamin E supplementation. In various other embodiments, the metabolic parameter that is regulated or the disease that is treated by administration of the formulation is not a parameter or disease recognized as treatable or known to be ameliorated by vitamin E supplementation of the subject.

Art-accepted assays for alteration in blood chemistry or metabolism are of use to confirm the efficacy of therapeutically relevant (or other) dosages of the particles of the invention. The following provide examples illustrating just some of the conventional assays that can be used to analyze the efficacy of the present invention in varying dosages. Standard assays for cytokines, insulin, lipid peroxidation and vitamin C, CRP, MCP-1, IL-6, TNF-a, leptin, VEGF, DPP-IV, retinol binding protein and insulin levels in the plasma can take the form of the sandwich ELISA method using commercially available kits from Fisher Thermo Scientific Co, Rockford, Ill. VEGF was measured using ELISA kit purchased from R and D system (Minneapolis, Minn.). DPPV-IV was measured using kit purchased from Cayman Chemical (Ann Arbor Mich.). Oxidative stress can be determined by measuring malondialdehyde (an end product of lipid peroxidation) by its reaction with thiobarbituric acid. See Jain, J. Biol. Chem. 264:21340-21345, 1989; Jain et al., Diabetes 38:1539-1543, 1989). Protein oxidation can be determined by the methods disclosed in Yan et al., Arch. Biochem Biophys. 327:330-334, 1996. Insulin resistance can for instance be determined by the HOMA method (Yaturu et al., Cytokine 34:219-23, 2006). Vitamin C concentration in the plasma can be determined by the method of Nino and Shaw. See Alan Wu (Ed). Teitz Clinical Guide to Laboratory Tests (Fourth Edition), Philadelphia, WB Saunders Co. 2006. Glycosylated hemoglobin can be determined using Glyco-Tek Affinity column kits and reagents (cat #5351) purchased from Helena Laboratories (Beaumont, Tex.). Glucose levels can be determined using glucose oxidase by Accu-check Advantage glucometer (Boehringer Manheim Corporation, Indianapolis, Ind.).

The effects on biological parameters of an exemplary formulation of the invention are forth in Table 1.

| Biomarker | 50-70% Octacosanol nanoparticle + TPGS | 95-100% Octacosanol nanoparticle + TPGS | Commercial Policosanol |
|---|---|---|---|
| Decreased ICAM-1 levels | yes | no | no |
| Plasmininogen activation inhibitor -1 (PAI-1) decrease | yes | no | no |
| Decreased Protein Oxidation | yes | yes | no |
| Increased Nitric oxide levels | yes | no | no |

-continued

| Biomarker | 50-70% Octacosanol nano-particle + TPGS | 95-100% Octacosanol nano-particle + TPGS | Commercial Policosanol |
|---|---|---|---|
| C-reactive protein reduction | yes | no | no |
| Retinal binding protein decrease | yes | no | no |
| Adiponectin increase | no | yes | no |
| MCP-1 reduction | yes | yes | no |
| Reduction in Insulin resistance | yes | yes | no |
| Fasting Plasma Insulin decrease | yes | yes | no |
| Vitamin C increase | yes | no | no |
| Fasting glucose reduction | no | yes | no |
| HbA1C reduction | yes | yes | no |
| Total Cholesterol decrease | no | yes | yes |
| Cholesterol/HDL decrease | yes | yes | yes |
| Triglycerides | no | yes | marginal effect |
| HDL increase | yes | yes | yes |
| Vascular endothelial growth factor | no | yes | no |
| DPP-IV | yes | no | no |

The following examples are given to illustrate the present invention. It should be understood, however, that the invention is not to be limited to the specific conditions or details described in these examples.

EXAMPLES

Example 1

Preparation of a Liquid Formulation Containing 1% Policosanol or Octacosanol

1. Prepare a water solution (100 mL) containing sucrose laureate (0.1-0.5%) and warm up to 80-85° C. under stirring.
2. In a beaker, weigh the policosanol or octacosanol (1 g) and at least one excipient or stabilizer (2-5 g) and warm up to 80-85° C. under stirring.
3. Pour the sugar ester solution into the beaker with policosanol or octacosanol and the excipient under strong stirring and keep at 80-85° C. for 5 min under stirring. When the temperature is below 50° C., the formulation becomes transparent.
4. Switch off the heater and keep under moderate stirring until room temperature is reached.
5. Add a preservative (e.g., potassium sorbate, sodium benzoate, citric acid anhydrous).
6. Put the solution into the bottles.

Example 2

Formulation Having 1% Policosanol or Octacosanol

| COMPONENT | % |
|---|---|
| Vitamin E TPGS | 4 |
| Policosanol or Octacosanol | 1 |
| Sugar ester | 0.95 |
| Potassium sorbate | 0.12 |
| Sodium benzoate | 0.2 |
| Citric acid anhydrous | 0.1 |
| Water | 93.63 |

Formulation Having 2% Policosanol or Octacosanol

| COMPONENT | % |
|---|---|
| Vitamin E TPGS | 6 |
| Policosanol or Octacosanol | 2 |
| Sugar ester | 0.92 |
| Glycerin | 0.12 |
| Potassium sorbate | 0.12 |
| Sodium benzoate | 0.2 |
| Citric acid anhydrous | 0.1 |
| Water | 90.54 |

Formulation Having 3% Policosanol or 3% Octacosanol

| COMPONENT | % |
|---|---|
| Vitamin E TPGS | 8 |
| Policosanol or Octacosanol | 3 |
| Sugar ester | 0.89 |
| Glycerin | 0.18 |
| Potassium sorbate | 0.12 |
| Sodium benzoate | 0.2 |
| Citric acid anhydrous | 0.1 |
| Water | 87.51 |

Example 3

Rat Studies using 1% solution of policosanol (10 mg/mL) with a particle size of 58 nm and ~57-58% octacosanol; and rat studies using 1% octacosanol (10 mg/mL) with a particle size of 56 nm and 98-99% octacosanol.

Materials and Methods

Male Zucker Diabetic Fatty rats were purchased at 5 weeks of age from Charles River Laboratories. The animals were randomly numbered and housed individually in plastic colony cages in a climate controlled animal facility. The animals were cared for in accordance with and use of generally accepted Committee protocols. Rats were allowed 2 days for environmental and trainer handling acclimation. The rats were tested for hyperglycemia by measuring their blood glucose concentration. The blood glucose was measured by tail incision using an advantage Accu-Chek® glucometer (Boehringer Mannheim Corp., Indianapolis, Ind.). The rats were randomly divided into 3 groups. Each rat in the treatment group was supplemented with appropriate dose of a nanoparticulate policosanol or octacosanol formulation of the invention daily for 8 weeks by oral gavage using 20 G feeding needles (Popper and Sons, New Hyde Park, N.Y.). The control group was supplemented with vehicle-buffer. Weight was monitored weekly to determine the policosanol supplementation dosage. The rats were maintained under standard housing conditions at 22±2° C. with 12:12-h light/dark cycles with a water and Purina 5008 lab chow diet ad libitum. At the end of 8 weeks, the rats were fasted overnight then euthanized for analysis by exposure to halothane (2-bromo-2-chloro-1,1,1-trifluoroethane). Blood was collected by puncturing the heart with a 19½ gauge needle and drawing the blood into a syringe containing heparin, then immediately transferring it to EDTA vacutainer tubes.

Policosanol

There were 3 groups of ZDF rats: 1. Controls-ZDF; 2.policosanol (2 mg per day/kg BW] supplemented ZDF, and (3) policosanol (5 mg per day/kg BW] supplemented ZDF at the start of the supplementation. This provided us the baseline level of all the parameters to be analyzed in the blood of ZDF rats.

Octacosanol:

There were 2 groups of ZDF rats: 1. Controls-ZDF; 2.policosanol (5 mg per day/kg BW] supplemented ZDF. This provided the baseline level of all the parameters to be analyzed in the blood of ZDF rats.

Rats were maintained on Purina 5008 diet with and without policosanol for 8 weeks. Blood samples were collected into pre-cooled EDTA-tubes kept in an ice bucket. EDTA-blood was used for HbAlc, and CBC assays (done by the clinical hematology laboratory). EDTA-blood was centrifuged. RBC was used for GSH and lipid peroxidation assay. The clear plasma was saved for lipid peroxidation and protein oxidation products and for TNF-α, IL-6, MCP-1, CRP, adipokines, VEGF, DPP-IV, insulin sensitivity by ELISA assays. All analyses were performed immediately after blood collection. Samples for oxidative stress markers and pro-inflammatory cytokines were stored in a −70° C. freezer. Complete chemistry profiles (CMP2) including SGOT and SGPT levels were also done to reveal any signs of toxicity during policosanol or octacosanol supplementation. In cytokine assays, control sera samples were analyzed at all times to monitor the variation from plate to plate and on different days of cytokine analyses. Assays were repeated if the variation in control serum values from day to day was greater than 7%.

Cytokines, insulin, lipid peroxidation and vitamin C assays: CRP, MCP-1, IL-6, TNF-a, leptin, retinol binding protein and insulin levels in the plasma were determined by the sandwich ELISA method using commercially available kits from Fisher Thermo Scientific Co, Rockford, Ill.). All appropriate controls and standards as specified by the manufacturer's kit were used. In the cytokine assay, control samples were analyzed each time to check the variation from plate to plate on different days of analysis. Oxidative stress was determined by measuring malondialdehyde (an end product of lipid per oxidation) by its reaction with thiobarbituric acid (1, 2). See Jain "Hyperglycemia can cause membrane lipid peroxidation and osmotic fragility in human red blood cells." J Biol Chem 264:21340-21345, 1989; and Jain et al. "Erythrocyte membrane lipid peroxidation and glycosylated hemoglobin in diabetes" Diabetes 38:1539-1543, 1989. Protein oxidation was determined by the methods of Yan et al. in "Efficacy of hypochlorous acid scavengers in the prevention of protein carbonyl formation" Arch Biochem Biophys 327:330-334, 1996. Insulin resistance was determined by HOMA method. See Yaturu et al. "Resistin and adiponectin levels in subjects with coronary artery disease and type 2 diabetes." Cytokine 34:219-23, 2006; and Ismael et al. "Blockade of sensory abnormalities and kinin B, receptor expression by N-acetyl-L-cysteine and ramipril in a rat model of insulin resistance." Eur J Pharmacol. 589:66-72, 2008. Vitamin C concentration in the plasma was determined by the method of Nino and Shaw. See Wu (ed). *Teitz Clinical Guide to Laboratory Tests* (Fourth Edition) Philadelphia, WB Saunders Co. 2006. GSH was determined by the method of Beutler in *Red Blood Cell Metabolism: A manual of Biochemical Methods* Pub: Grune and Stratton, N.Y. 131-134, 1984.

Measurement of Glycosylated Hemoglobin (GHb), Glucose and Insulin Resistance:

Glycosylated hemoglobin was determined using Glyco-Tek Affinity column kits and reagents (cat #5351) purchased from Helena Laboratories (Beaumont, Tex.). Glucose levels were determined using glucose oxidase by Accu-check Advantage glucometer (Boehringer Manheim Corporation, Indianapolis, Ind.).

All chemicals were purchased from Sigma Chemical Co. (St. Louis, Mo.) unless otherwise mentioned.

Data analysis: Data was analyzed using ANOVA between different groups with Sigma Plot statistical software (Jandel Scientific, San Rafael, Calif.). A p value of less than 0.05 was considered significant.

Results

No difference was observed in the body weight at the time of sacrifice between different treatment groups. The weekly intake of diet by each rat, as assessed at 5 and 7 weeks after start of supplementation, was similar in both the groups. The body weight and food intake for the male Zucker-Fatty rats supplemented with policosanol for 8 weeks are provided in Table 2 below. Each value represents the mean±SE.

TABLE 2

|  | N units | Body Weight @ Sacrifice g | Food Intake 5 wks g/day | Food Intake 7 wks g/day |
|---|---|---|---|---|
| Diabetic | 7 | 370.57 ± 3.92 | 37.86 ± 0.73 | 38.18 ± 1.17 |
| 2 mg/kg Policosanol | 6 | 354.33 ± 9.65 | 35.00 ± 0.57 | 35.67 ± 1.56 |
| 5 mg/kilo Policosanol | 6 | 364.33 ± 5.74 | 37.43 ± 1.09 | 36.00 ± 1.35 |

Figure 30:
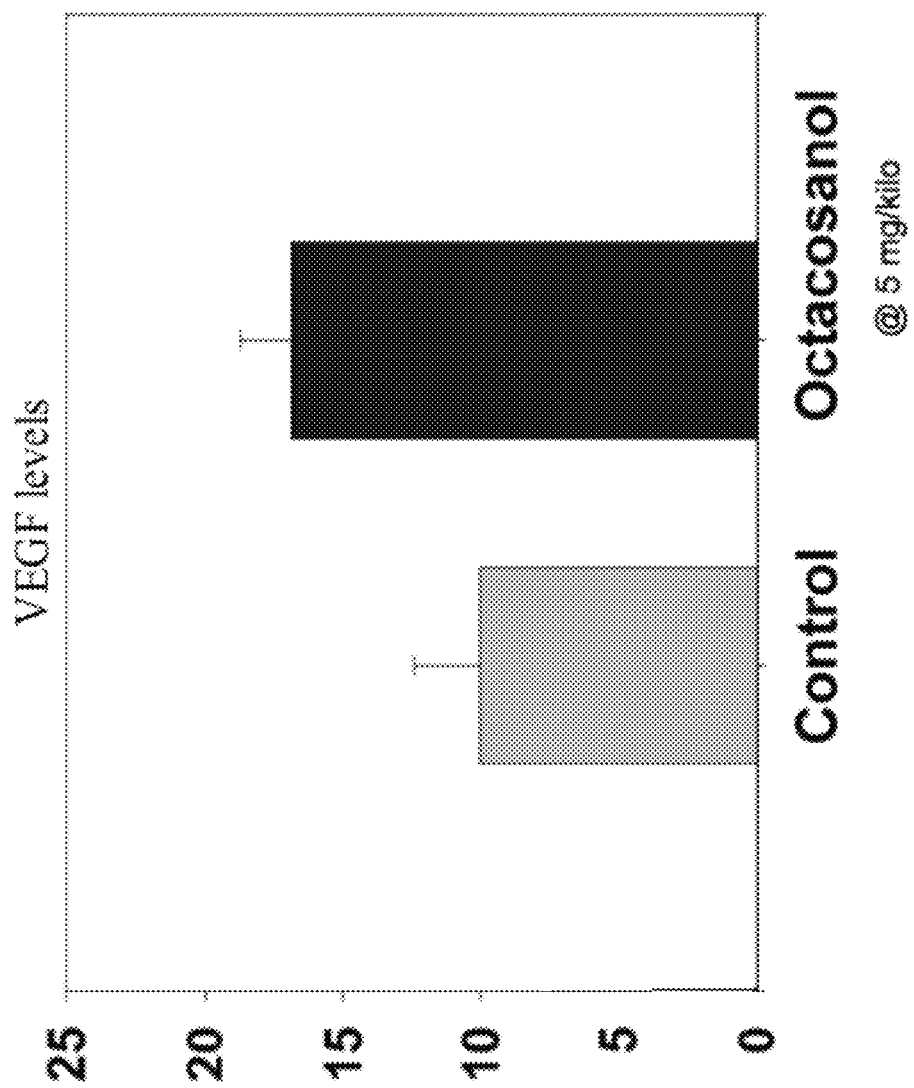
FIG. 30 shows VEGF (vascular endothelial growth factor) levels in untreated rats and rats treated with particles of the invention at 5 mg/kg.
Figure 31:
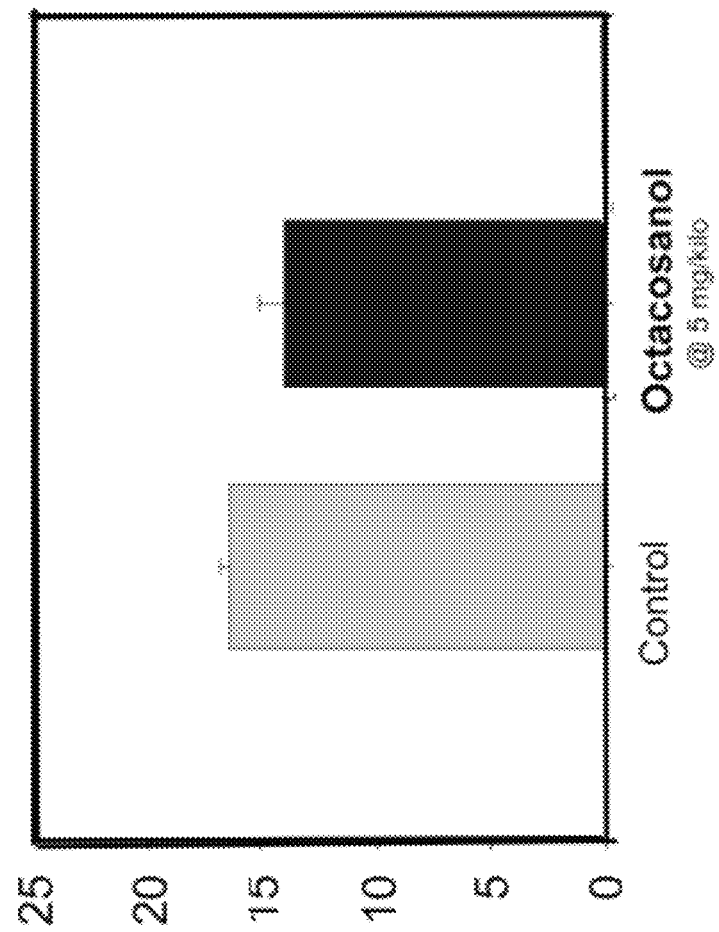
FIG. 31 shows Glycated Hemoglobin levels in untreated and treated rats with particles of invention at 5 mg/kg

In all the figures, values marked '*' are statistically significant compared with controls ($p<0.05$). FIG. 30 provides data on alanine aminotransferase (ALT), alkaline phosphatase (AP), aspartate aminotransferase (AST), blood urea nitrogen (BUN), creatinine and anion Gap levels in the blood of supplemented rats. Analysis of results demonstrate that policosanol supplementation lowered blood levels of, protein oxidation, MCP-1 and CRP and, and increased blood levels of vitamin C. While policosanol did not change blood levels of transaminases, Table II shows that policosanol supplementation did not affect hemoglobin, hematocrit or RBC counts in diabetic rats, which rules out any effect of altered red cell survival on lower glycosylated hemoglobin levels in policosanol supplemented ZDF rats and affirm lack of any sign of toxicity in policosanol supplemented rats. The data demonstrates that policosanol supplementation does not appear to cause any toxicity as assessed by liver function or renal function tests.

TABLE 3

Effects of policosanol on blood hemoglobin, hematocrit, and red blood cell counts in Zucker Fatty Rats. Each value represents the mean ± SE

| | N | RBC ($10^6$/μL) | Hemoglobin (g/dL) | Hematocrit (%) |
|---|---|---|---|---|
| Diabetic | 7 | 9.48 ± 0.13 | 15.96 ± 0.23 | 48.54 ± 0.78 |
| 2 mg/kilo policosanol | 7 | 8.91 ± 0.22 | 15.02 ± 0.33 | 45.30 ± 1.01 |
| 5 mg/kilo policosanol | 5 | 8.82 ± 0.20 | 14.97 ± 0.44 | 45.28 ± 1.10 |

TABLE 4

WBC

| | N | WBC (k/μL) | Mean Corpuscular Volume (fL) | Mean Corpuscular Hemoglobin (pg) | Mean Corpuscular Concentration (g/dL) |
|---|---|---|---|---|---|
| Diabetic | 7 | 5.77 ± 0.53 | 51.17 ± 0.17 | 16.86 ± 0.05 | 32.90 ± 0.13 |
| 2 mg/kilo Policosanol | 6 | 6.80 ± 0.35 | 50.85 ± 0.31 | 16.87 ± 0.18 | 33.13 ± 0.33 |
| 5 mg/kilo Policosanol | 6 | 6.40 ± 0.32 | 51.33 ± 0.17 | 16.95 ± 0.14 | 33.02 ± 0.23 |

TABLE 5

Platelet counts and WBC segmented

| | N | Platelet Count (k/μL) | Absolute Banded Neutrophils (K/μL) | Lymphocyte (K/μL) | Monocyte (K/μL) | Eosinophil (K/μL) | Basophil (K/μL) |
|---|---|---|---|---|---|---|---|
| Diabetic | 7 | 910.00 ± 45.74 | 32.08 ± 1.18 | 59.56 ± 3.43 | 0.12 ± 0.40 | 1.73 ± 0.20 | 2.27 ± 1.43 |
| 2 mg/kilo Policosanol | 6 | 892.50 ± 55.95 | 42.52 ± 5.41 | 52.45 ± 7.49 | 0.08 ± 0.04 | 1.72 ± 0.31 | 0.32 ± 0.06 |
| 5 mg/kilo policosanol | 6 | 864.33 ± 75.66 | 45.50 ± 4.74 | 49.62 ± 6.50 | 0.24 ± 0.12 | 1.20 ± 0.28 | 1.05 ± 0.42 |

TABLE 6

Clinical chemistry results of male Zucker-Fatty rats supplemented with Policosanol for 8 weeks

| | N | AP (u/L) | BUN (mg/dL) | CRT (mg/dL) | AST (u/L) | ALT (u/L) | Total Bilirubin (mg/dL) | Anion Gap (μ/L) | BUN/CRT Ratio (mMol/L) |
|---|---|---|---|---|---|---|---|---|---|
| Diabetic | 7 | 24.00 ± 4.91 | 16.86 ± 0.83 | 0.40 ± 0.00 | 173.00 ± 31.86 | 99.57 ± 6.38 | 0.06 ± 0.02 | 28.00 ± 1.85 | 42.57 ± 2.11 |
| 2 mg/Kilo Policosanol | 6 | 26.00 ± 5.13 | 20.00 ± 2.18 | 0.42 ± 0.02 | 128.80 ± 11.51 | 128.50 ± 19.95 | 0.10 ± 0.00 | 25.33 ± 1.52 | 47.67 ± 3.24 |
| 5 mg/kilo policosanol 6751 | 6 | 23.33 ± 5.12 | 19.20 ± 1.07 | 0.43 ± 0.03 | 152.00 ± 5.50 | 140.50 ± 16.11 | 0.07 ± 0.02 | 27.33 ± 0.67 | 48.20 ± 2.71 |

Each value represents the mean ± SE;
AP: Alkaline phosphatase;
BUN: Blood Urea Nitrogen;
CRT: Creatinine;
AST: Aspartate Aminotransferase;
ALT: Alanine Aminofererase.

The liver plays a major role in the regulation of glucose metabolism. See Michael et al. "Loss of Insulin signaling in hepatocytes leads to severe insulin resistance and progressive hepatic dysfunction." Mol. Cell. 6:87-97, 2000. The liver is a storage organ for glucose, proteins and vitamins. The glycogenic and gluconeogenic pathways which are major regulators of blood glucose levels are unique to liver. Several hormones, including insulin, glucagon, growth hoimone, cortisol, and catecholamines contribute to the regulation of glucose metabolism by the liver.

In conclusion, policosanol supplementation has the potential to lower blood levels of insulin resistance and the pro-inflammatory cytokines and increase in vitamin C levels.

Results: Octacosanol

No difference was observed in the body weight at the time of sacrifice between different treatment groups. The weekly intake of diet by each rat, as assessed at 7 weeks after start of supplementation, was similar in both the groups. The body weight and food intake for the male Zucker-Fatty rats supplemented octacosanol for 7 weeks are provided in Table 7 below. Each value represents the mean±SE.

TABLE 7

Body weight and food intake for male Zucker-Fatty rats supplemented with octacosanol

|  | N | Body Weight at Sacrifice Day (g) | Food intake 7 wks. (g/day) |
|---|---|---|---|
| Diabetic | 6 | 345.00 ± 7.76 | 40.93 ± 3.88 |
| Octacosanol | 5 | 338.80 ± 5.71 | 39.52 ± 1.25 |

TABLE 8

Clinical chemistry results of male Zucker-Fatty rats supplemented with Octacosanol

|  | N | AP (u/L) | BUN (mg/dL) | CRT (mg/dL) | AST (u/L) | ALT (u/L) | Total Bilirubin (mg/dL) | Anion gap (μ/L) | BUN/CRT ratio (mMol/L) |
|---|---|---|---|---|---|---|---|---|---|
| Diabetic | 6 | 43.20 ± 6.69 | 19.40 ± 1.25 | 0.34 ± 0.04 | 116.00 ± 12.12 | 137.75 ± 16.51 | 0.14 ± 0.04 | 20.80 ± 1.46 | 59.66 ± 6.40 |
| Octacosanol | 5 | 34.40 ± 4.66 | 17.00 ± 0.95 | 0.30 ± 0.05 | 160.20 ± 21.93 | 162.80 ± 20.29 | 0.10 ± 0.00 | 18.60 ± 0.51 | 62.34 ± 8.97 |

Each value represents the mean ± SE;
AP: Alkaline phosphatase;
BUN: Blood Urea Nitrogen;
CRT: Creatinine;
AST: Aspartate Aminotransferase;
ALT: Alanine Aminotranserease.

TABLE 9

Hematology results of male Zucker-Fatty rats supplemented with Octacosanol

|  | N | RBC ($10^6$/μL) | Hemoglobin (g/dL) | Hematocrite (%) |
|---|---|---|---|---|
| Diabetic | 6 | 8.37 ± 0.25 | 15.32 ± 0.48 | 43.92 ± 1.34 |
| Octacosanol | 5 | 8.67 ± 0.34 | 15.42 ± 0.49 | 45.60 ± 1.76 |

|  | N | Mean Corpuscular Volume (fL) | Mean Corpuscular Hemoglobin (pg) | Mean Corpuscular Concentration (g/dL) | Platelet Count (k/μL) |
|---|---|---|---|---|---|
| Diabetic | 6 | 52.47 ± 0.38 | 18.30 ± 0.14 | 34.9 ± 0.29 | 883.83 ± 64.46 |
| Octacosanol | 5 | 52.56 ± 0.86 | 17.76 ± 0.09 | 33.84 ± 0.20 | 823.00 ± 61.68 |

|  | N | Absolute Banded Neutrophils (κ/μL) | Lymphocyte (κ/μL) | Monocyte (κ/μL) | Eosinophil (κ/μL) | Basophil (κ/μL) |
|---|---|---|---|---|---|---|
| Diabetic | 6 | 0.76 ± 0.81 | 2.37 ± 1.02 | 0.02 ± 0.02 | 0.01 ± 4.79e–3 | 0.97 ± 0.69 |
| Octacosanol | 5 | 0.91 ± 0.50 | 1.88 ± 0.46 | 0.04 ± 0.02 | 0.20 ± 0.20 | 0.71 ± 0.32 |

Table 7 provides data on alanine aminotransferase (ALT alkaline phosphatase (AP), aspartate aminotransferase (AST), blood urea nitrogen (BUN), creatinine and anion Gap levels in the blood of supplemented rats. Analysis of results demonstrates that octacosanol supplementation lowered blood levels of protein oxidation, effected a large increase in adiponectin levels, MCP-1, and increas in VGEF and Insulin resistance and fasting blood glucose triglycerides and, under the dosage conditions, did not affect IL-6, TNF alpha and RBP-4. While policosanol did not change blood levels of transaminases, Table 9 shows that octacosanol supplementation did not affect hemoglobin, hematocrit or RBC counts in diabetic rats, which rules out any effect of altered red cell survival on lower glycosylated hemoglobin levels in octacosanol supplemented ZDF rats and affirms lack of any sign of toxicity in octacosanol supplemented rats. The data demonstrates that policosanol supplementation does not appear to cause any toxicity as assessed by liver function or renal function tests.

In conclusion, octacosanol supplementation has the potential to lower blood levels of insulin resistance and, decrease levels of pro inflammatory cytokines increase levls of VEGF (vascular endothelial growth factor).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A composition comprising nanoparticles of policosanol, wherein each nanoparticle comprises:
   (a) a policosanol fraction comprising about 50% to 69% octacosanol; and
   (b) a stabilizer fraction comprising tocopheryl polyethylene glycol (1000) succinate ("TPGS"), wherein the ratio of octacosanol:stabilizer fraction ranges from about 1:1.6 to about 1:3.5 and the nanoparticles have a size between about 40 nm and about 100 nm in diameter and wherein at least 99% of the nanoparticles have a particle size of less than about 70 nm as determined by a light scattering method.

2. The composition of claim 1, wherein said policosanol fraction further comprises triacontanol.

3. The composition of claim 2, wherein said nanoparticle has a ratio of octacosanol:triacontanol of from about 2:1 to about 7:1.

4. The composition of claim 2, wherein said nanoparticle has a ratio of octacosanol:hexacosanol of from about 4:1 to about 8:1.

5. The composition of claim 1, wherein said nanoparticle has a size of about 60 nm in diameter.

6. The composition of claim 1, further comprising a pharmaceutically acceptable carrier.

7. The composition of claim 6, said composition being a unit dosage formulation comprising—from about 10 to about 30 mg/mL (wt/vol) of said nanoparticles.

8. A composition comprising nanoparticles of octacosanol, wherein each nanoparticle comprises:
   (a) a policosanol fraction comprising about 95% to 100% octacosanol; and
   (b) a stabilizer fraction comprising tocopheryl polyethylene glycol (1000) succinate ("TPGS"), wherein the ratio of octacosanol:stabilizer fraction ranges from about 1:1.6 to about 1:3.5 and the nanoparticles have a size between about 40 nm and about 100 nm in diameter and wherein at least 99% of the nanoparticles have a particle size of less than about 70 nm as determined by a light scattering method.

9. The composition of claim 8, wherein said policosanol fraction further comprises: triacontanol.

10. The composition of claim 8, wherein said nanoparticle has a ratio of octacosanol:triacontanol of from about 45:1 to about 100:1.

11. The composition of claim 8, wherein said nanoparticle has a ratio of octacosanol:hexacosanol of from about 45:1 to about 100:1.

12. The composition of claim 8, wherein said nanoparticle has a size of about 60 nm in diameter.

13. The composition of claim 8, further comprising a pharmaceutically acceptable carrier.

14. The composition of claim 13, said composition being a unit dosage formulation comprising from about 10 to about 30 mg/mL (wt/vol) of said nanoparticles.

* * * * *